United States Patent [19]

Gimeno et al.

[11] Patent Number: 5,948,639
[45] Date of Patent: Sep. 7, 1999

[54] TGF-β PATHWAY GENES

[75] Inventors: Carlos J. Gimeno; Dean A. Falb, both of Wellesley, Mass.

[73] Assignee: Millennium Pharmaceuticals, Inc., Cambridge, Mass.

[21] Appl. No.: 08/844,312

[22] Filed: Apr. 10, 1997

[51] Int. Cl.$^6$ ............ C12P 21/00; C07H 21/04; C07K 14/46
[52] U.S. Cl. ............ 435/69.1; 435/69.7; 435/252.3; 435/320.1; 435/325; 530/350; 536/23.1; 536/23.4; 536/23.5
[58] Field of Search ................ 435/69.1, 69.7, 435/325, 252.3, 320.1; 536/23.1, 23.4, 23.5; 530/350

[56] References Cited

PUBLICATIONS

Chen H I; Sudol M. The WW domain of Yes–associated protein binds a proline–rich ligand that differs from the consensus established for Src homology 3–binding modules. Proc Natl. Acad Sci U S A, (Aug. 15, 1995) 92 (17) 7819–23.
Ventura et al. Interaction of transforming growth factor–beta receptor I with farnesyl–protein transferase–alpha in yeast and mammailian cells. J. Biol Chem,(Jun. 14, 1996) 271 (24) 13931–4, Jun. 1996.
George et al, "Current methods in sequence comparison and analysis," in Macromolecular Sequencing and Synthesis, Selected Methods and Applications, 1988, D.H. Schlesinger (ed.), Alan R. Liss, Inc., New York, NY, pp. 127–149.
Barton, "Protein sequence alignment and database scanning," in Protein Structure Prediction, A Practical Approach, 1996 IRL Press at Oxford University Press, Oxford, UK, pp. 31–63.
Sambrook et al. Molecular Cloning: A Laboratory Manual Second Edition vols. 1, 2 and 3. Cold Spring Harbor Laboratory Press: Cold Spring Harbor, New York, U.S.A. Nov., 1989.
Bowie et al. Deciphering the message in protein sequences: tolerance to amino acid substitutions, Science, (Mar. 16, 1990) 247 (4948) 1306–10.
GenBank Accesion No. W66992, Natioanl Libray of Medcine, Bethesda, MD. Marra et al. The WashU–HHMI Mouse EST Project. Jun. 14, 1996.
Daniel et al. Virology, (Aug. 1, 1994) 202 (2) 540–549.
Baker, J. et al., "A Novel Mesoderm Inducer, Madr2, Functions in the Activin Signal Transduction Pathway", *Genes & Development*, vol. 10, pp. 1880–1889 (1996).
Chen, Y. et al., "Regulation of Transforming growth factor β–and Activin–Induced Transcription by Mammalian Mad Proteins", *PNAS*, vol. 93, pp. 12992–12997 (1996).
Graff, J. et al., "Xenopus Mad Proteins Transduce Distinct Subsets of Signals for the TGFβ Superfamily", *Cell*, vol. 85, pp. 479–487 (1996).
Hahn, S. et al., "Homozygous Deletion Map at 18q21.1 in Pancreatic Cancer", *Cancer Research*, vol. 56, pp. 490–494 (1996).
Hoodless, P. et al., "MADR1, a MAD–Related Protein That Functions in BMP2 Signaling Pathways", *Cell*, vol. 85, pp. 489–500 (1996).
Meersseman, G. et al., "The C–Terminal Domain of Mad–like Signal Transducers is Sufficient for Biological Activity in the Xenopus Embryo and Transcriptional Activation", *Mechansisms of Development*, vol. 61, pp. 127–140 (1997).
Riggins, G. et al., "Mad–Related Genes in the Human", *Nature Genetics*, vol. 13, pp. 347–349 (1996).
Savage, C. et al., "*Caenorhabditis elegans* Genes sma–2, sma–3, sma–4 Define a Conserved Family of Transforming Growth Factor β Pathway Components", *PNAS*, vol. 93, pp. 790–794 (1996).
Sekelsky, J. et al., "Genetic Characterization and Cloning of Mothers against dpp, a Gene Required for decapentaplegic Function *Drosophila melanogaster*", *Genetics*, vol. 139, pp. 1347–1358 (1995).
Thomsen, G. "Xenopus Mothers Against Decapentaplegic is an Embryonic Ventralizing Agent that Acts Downstream of the BMP–2/4 Receptor", *Development*, vol. 122, pp. 2359–2366 (1996).
Wilson, R. et al., "2.2 Mb of contiguous Nucleotide Sequnece from Chromosome III of *C. Elegans*", *Nature*, vol. 368, pp. 32–38 (1994).
Yingling, J. et al., "Mammalian Dwarfins are Phosphorylated in Response to Transforming Growth Factor β and are implicated in Control of Cell Growth", *PNAS*, vol. 93, pp. 8940–8944 (1996).
Zhang, Y. et al., "Receptor–Associated Mad Homologues Synergize as Effectors of the TGF–β Response", *Nature*, vol. 383, pp. 168–172 (1996).
Zhao, G. et al., "Evidence that Mothers–against–dpp–related 1 (Madr 1) plays a role in the Initiation and Maintenance of Spermatogenesis in the Mouse" *Mechanisms of Development*, vol. 61, pp. 63–73 (1997).
GenBank™ Accession Number U73825 for Human MAD–like Protein mRNA, complete cds.
GenBank™ Acession Number U79748 for Mus musculus deletion target in pancreatic carcinoma 4 Homolog (DPC4) mRNA, complete cds.
GenBank™ Accession Number AA051144 for The WashU–HHMI Mouse EST Project, Marra et al. Sep. 09, 1996.

*Primary Examiner*—Elizabeth Kemmerer
*Assistant Examiner*—David Romeo
*Attorney, Agent, or Firm*—Lahive & Cockfield, LLP; Amy E. Mandragouras

[57] ABSTRACT

The invention provides isolated nucleic acids molecules, designated EMI1 nucleic acid molecules, which encode proteins involved in growth factor, e.g., TGF-β, cell signaling. The invention also provides antisense nucleic acid molecules, recombinant expression vectors containing EMI1 nucleic acid molecules, host cells into which the expression vectors have been introduced, and nonhuman transgenic animals in which an EMI1 gene has been introduced or disrupted. The invention still further provides isolated EMI1 proteins, fusion proteins, antigenic peptides and anti-EMI1 antibodies. Diagnostic, screening, and therapeutic methods utilizing compositions of the invention are also provided.

17 Claims, 2 Drawing Sheets

```
TGCGGGCGGT GGAAGGCGGA AGTAGGAGAG GAGTTCGGCG CCGCTTCTGT GGCCACGGCA              60

GCTTCACGGT GATGAT ATG GCA TCT GCC AGC TCT AGC CGG GCA GGA GTG GCC CTG CCT TTT  121
               M   A   S   A   S   S   S   R   A   G   V   A   L   P   F      15

GAG AAG TCT CAG CTC ACT TTG AAA GTG GTG TCC GCA AAG CCC AAG GTG CAT AAT CGT CAA  181
 E   K   S   Q   L   T   L   K   V   V   S   A   K   P   K   V   H   N   R   Q   35

CCG CGA ATT AAC TCC TAC GTG GAG GTG GCG GTG GAT GGA CTC CCC AGT GAG ACC AAG AAG  241
 P   R   I   N   S   Y   V   E   V   A   V   D   G   L   P   S   E   T   K   K   55

ACT GGG AAG CGC ATT GGG AGC TCT GAG CTT CTC TGG AAT GAG ATC ATC ATT TTG AAT GTT ACG 304
 T   G   K   R   I   G   S   S   E   L   L   W   N   E   I   I   I   L   N   V   T  76

GCA CAG AGT CAT TTA GAT TTA AAG GTC TGG AGC TGC CAT ACC TTG AGA AAT GAA CTG CTA GGC 367
 A   Q   S   H   L   D   L   K   V   W   S   C   H   T   L   R   N   E   L   L   G  97

ACC GCA TCT GTC AAC CTC TCC AAC GTC TTG AAG AAC AAT GGG GGC AAA ATG GAG AAC ATG   427
 T   A   S   V   N   L   S   N   V   L   K   N   N   G   G   K   M   E   N   M    117

CAG CTG ACC CTG AAC CTG CAG ACG GAG AAC AAA GGC AGC GTT GTC TCA GGC GGA GAG CTG   487
 Q   L   T   L   N   L   Q   T   E   N   K   G   S   V   V   S   G   G   E   L    137

ACA ATT TTC CTG GAC GGG CCA ACT GTT GAT CTG GGA AAT GTG CCT AAT GGC AGT GCC CTG ACA 550
 T   I   F   L   D   G   P   T   V   D   L   G   N   V   P   N   G   S   A   L   T 158

GAT GGA TCA CAG CTG CCT TCG AGA GAC TCC AGT GGA ACA GCA GTA GCT CCA GAG AAC CGG   610
 D   G   S   Q   L   P   S   R   D   S   S   G   T   A   V   A   P   E   N   R    178

CAC CAG CCC CCC AGC ACA AAC TGC TTT GGT GGA AGA TCC CGG ACG CAC AGA CAT TCG GGT GCT 673
 H   Q   P   P   S   T   N   C   F   G   G   R   S   R   T   H   R   H   S   G   A 199

TCA GCC AGA ACA ACC CCA GCA ACC GGC GAG CAA AGC CCC GGT GCT CGG AGC CGG CAC CGC   733
 S   A   R   T   T   P   A   T   G   E   Q   S   P   G   A   R   S   R   H   R    219

CAG CCC GTC AAG AAC TCA GGC CAC AGT GGC TTG GCC AAT GGC ACA GTG AAT GAT GAA CCC   793
 Q   P   V   K   N   S   G   H   S   G   L   A   N   G   T   V   N   D   E   P    239

ACA ACA GCC ACT GAT CCC GAA GAA CCT TCC GTT GTT GGT GTG ACG TCC CCA CCT GCT GCA CCC 856
 T   T   A   T   D   P   E   E   P   S   V   V   G   V   T   S   P   P   A   A   P 260

TTG AGT GTG ACC CCG AAT CCC AAC ACG ACT TCT CTC CCT GCC CCA GCC ACA CCG GCT GAA   916
 L   S   V   T   P   N   P   N   T   T   S   L   P   A   P   A   T   P   A   E    280

GGA GAG GAA CCC AGC ACT TCG GGT ACA CAG CAG CTC CCA GCG GCT GCC CAG GCC CCC GAC   976
 G   E   E   P   S   T   S   G   T   Q   Q   L   P   A   A   A   Q   A   P   D    300

GCT CTG CCT GCT GGA TGG GAA CAG CGA GAG CTG CCC AAC GGA CGT GTC TAT TAT GTT GAC  1036
 A   L   P   A   G   W   E   Q   R   E   L   P   N   G   R   V   Y   Y   V   D    320
```

```
CAC AAT ACC AAG ACC ACC ACC TGG GAG CGG CCC CTT CCT CCA GGG TAG GTCATCAACT      1094
 H   N   T   K   T   T   T   W   E   R   P   L   P   P   G   *                  335

GAGAAGACCT GAGACTCTGG AACTGACACC ATGAGTCACC CAATGGCTTC TTGAAACGGT                1154

CCCTTTCTGC GGAGGTAGCA TAGCACAGTG ACGTTTATTC CGGGTCACTT GATTGCTTTT                1214

CCTATCCACT TACCTTAATA TTGCTCCCAT GTCTTAGGAC ATATTAGAAT TATTAGAAGA                1274

TCTCTGGGAA ACAAAA                                                                1290
```

TGF-β PATHWAY GENES

BACKGROUND OF THE INVENTION

The transforming growth factor-β(TGF-β) family of proteins consists of a number of related, but functionally distinct, proteins (Barnard, J. A. et al. (1990) *Biochim. Biophys. Acta.* 1032:79–87; Roberts, A. B. and Sporn, M. B. eds. The Transforming Growth Factor-βs in Peptide Growth Factors and Their Receptors. I. Handbook of Experimental Pharmacology, vol. 95/I (Springer-Verlag, Berlin, 1990) 419–472). One member of the TGF-β family of proteins, TGF-β1, is a multifunctional cytokine with both growth promoting and inhibiting activities. Recently, TGF-β1 has been found to play a role in modulating repair of vascular injuries such as restenosis lesions (Nikol, S. et al. (1992) *J. Clin. Invest.* 90:1582–1592) and atherosclerotic plaques (Kojima, S. et al. (1991) *J. Cell Biol.* 113(6):1439–1445.

Members of the TGF-β family of proteins initiate cell signaling by binding to heteromeric receptor complexes of type I (TβRI) and type II (TβRII) serine/threonine kinase receptors (reviewed by Massagué, J. et al. (1994) *Trends Cell Biol.* 4:172–178; Miyazono, K. et al. (1994) *Adv. Immunol.* 55:181–220). Activation of this heteromeric receptor complex occurs when TGF-β binds to TβRII, which then recruits and phosphorylates TβRI. Activated TβRI then propagates the signal to downstream targets (Chen, F. and Weinberg, R. A. (1995) *PNAS* 92:1565–1569; Wrana, J. L. et al. (1994) *Nature* 370:341–347).

Until recently, the proteins involved in the intracellular TGF-βsignaling pathway were largely unknown. In 1995, however, a protein from *Drosophila melanogaster*, named Mothers against dpp ("MAD"), was cloned and found to be required for cell signaling by the TGF-β family member decapentaplegic (dpp) (Sekelsky, J. J. et al. (1995) *Genetics* 139:1347–1358). Subsequently, cDNAs for four human homologues of the MAD protein, named hMAD1–4 and now generally known as MAD-related (MADR) proteins, were isolated and at least two of which (hMAD-3 and hMAD-4) were characterized as effectors of TGF-β cellular responses (Zhang, Y. et al. (1996) *Nature* 383:168–172). hMAD-1 corresponds to MADR1, a tumor suppressor, whose inactivation may play a role in colorectal cancer (Eppert, K. et al. (1996) *Cell* 86:543–552). hMAD-4 is identical to DPC4, a candidate tumor suppressor, whose inactivation may play a role in pancreatic and other human cancers (Hahn, S. A. et al. (1996) *Science* 271:350–353). Once a cell is activated by a member of the TGF-β family of proteins, activated MADR proteins or complexes of MADR proteins may be translocated into the nucleus to function as a transcriptional activator(s). Thus, as members of the TGF-β family initiate a variety of beneficial effects on various cell types, e.g., epithelial cells and endothelial cells, it is desirable to modulate TGF-β effects on such cells. One method of modulating TGF-β initiated cell function is to modulate the function of proteins, such as the MADR proteins, which are involved in propagating the TGF-β signal in the cell.

SUMMARY OF THE INVENTION

This invention provides a novel nucleic acid molecule which encodes a protein, referred to herein as Endothelial MAD Interactor 1 ("EMI1") protein, which is capable of, for example, modulating the activity of proteins involved in the TGF-β signaling pathway to thereby modulate the effects of TGF-β on TGF-β responsive cells. Nucleic acid molecules encoding an EMI1 protein are referred to herein as EMI1nucleic acid molecules. In a preferred embodiment, the EMI1 protein interacts with (e.g., binds to) a protein which is a member of the MADR family of proteins. Examples of such proteins include Drosophila MAD, human MADR6 (also known as the fchd534 gene product) and human MADR7 (also known as the fchd540 gene product). MADR6 and MADR7 are described in U.S. Ser. Nos. 08/599,654 and 08/799,910, respectively, the contents of which are expressly incorporated herein by reference.

MADR6 and MADR7 proteins are expressed in endothelial cells, are known to interact with one another, and are up-regulated in endothelial cells in a model of shear stress conditions. It has also been found that MADR6 and MADR7 inhibit TGF-β signaling in endothelial cells. As TGF-β signaling of endothelial cells is involved in repair of vascular injuries and MADR6 and MADR7 have been found to inhibit this TGF-β initiated activity in endothelial cells, MADR6 and MADR7 are good targets for modulating TGF-β initiated repair of vascular injuries. The EMI1 protein of the present invention binds to MADR6 and MADR7 and modulates their activity. Thus, EMI1 molecules can be used to modulate TGF-β initiated repair of vascular injuries and thus to treat cardiovascular disorders.

In addition, MADR proteins function in other cell types, e.g., epithelial cells, gut-derived epithelial cells such as epithelial cells of the pancreas and colon, to mediate TGF-β signaling. For example, MADR1 mediates TGF-β tumor suppressor effects in gut-derived epithelial cells. Thus, proteins, such as EMI1, which modulate the activity of MADR1, are also useful in the treatment of cancers, e.g., epithelial cell cancers such as colorectal carcinomas.

Accordingly, one aspect of the invention pertains to isolated nucleic acid molecules (e.g., cDNAs) comprising a nucleotide sequence encoding an EMI1 protein or biologically active portions thereof, as well as nucleic acid fragments suitable as primers or hybridization probes for the detection of EMI1-encoding nucleic acid (e.g., mRNA). In particularly preferred embodiments, the isolated nucleic acid molecule comprises the nucleotide sequence of SEQ ID NO:1, the nucleotide sequence of the DNA insert of the plasmid deposited with ATCC as Accession Number 98375, or the coding region or a complement of either of these nucleotide sequences. In other particularly preferred embodiments, the isolated nucleic acid molecule of the invention comprises a nucleotide sequence which hybridizes to or is at least about 60–65%, preferably at least about 7075%, more preferably at least about 80–85%, and even more preferably at least about 9095% or more homologous to the nucleotide sequence shown in SEQ ID NO:1, the nucleotide sequence of the DNA insert of the plasmid deposited with ATCC as Accession Number 98375, or a portion of either of these nucleotide sequences. In other preferred embodiments, the isolated nucleic acid molecule encodes the amino acid sequence of SEQ ID NO:2 or an amino acid sequence encoded by the nucleotide sequence of the DNA insert of the plasmid deposited with ATCC as Accession Number 98375. The preferred EMI1 proteins of the present invention also preferably possess at least one of the EMI1 activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2, e.g., sufficiently homologous to an amino acid sequence of SEQ ID NO:2 such that the protein or portion thereof maintains an EMI1 activity. Preferably, the protein or portion thereof encoded by the nucleic acid molecule maintains the ability to modulate a TGF-β response in a TGF-β responsive cell. In one embodiment, the protein encoded by the nucleic acid molecule is at least about 60–70%, preferably at least about 80–85%, and more preferably at least about 86, 88, 90%, and most preferably at least about 90–95% or more homologous to the amino acid sequence of SEQ ID NO:2 (e.g., the entire amino acid sequence of SEQ ID NO:2) or the amino acid sequence encoded by the nucleotide sequence of the DNA insert of the plasmid deposited with ATCC as Accession Number 98375. In another preferred embodiment, the protein is a full length human protein which is substantially homologous to the entire amino acid sequence of SEQ ID NO:2 (encoded by the open reading frame shown in SEQ ID NO:3).

In yet another embodiment, the isolated nucleic acid molecule is derived from a human and encodes a portion of a protein which includes a WW domain. Preferably, the WW domain encoded by the human nucleic acid molecule is at least about 55%, preferably at least about 60–65%, even more preferably at least about 70–75%, and most preferably at least about 80–90% or more homologous to the WW domain (i.e., amino acid residues 300–335) of SEQ ID NO:2 which is shown as a separate sequence designated SEQ ID NO:4. In still another embodiment, the nucleic acid molecule is a nonmammalian molecule which encodes a WW domain. Preferably, the WW domain encoded by the nonmammalian nucleic acid is at least about 75%, more preferably at least about 80–85%, and most preferably at least about 90–95% or more homologous to SEQ ID NO:4.

In another preferred embodiment, the isolated nucleic acid molecule is derived from a human and encodes a protein (e.g., an EMI1 fusion protein) which includes a WW domain which is at least about 55% or more homologous to SEQ ID NO:4 and has one or more of the following activities: 1) it can interact with (e.g., bind to) an MADR protein; 2) it can modulate the activity of an MADR protein; 3) it can interact with (e.g., bind to) a protein having a PY motif, 4) it can modulate the activity of a protein having a PY motif; and 5) it can modulate a TGF-β response in a TGF-β responsive cell (e.g., an epithelial cell or an endothelial cell) to, for example, beneficially affect the TGF-β responsive cell.

In another embodiment, the isolated nucleic acid molecule is at least 15 nucleotides in length and hybridizes under stringent conditions to a nucleic acid molecule comprising the nucleotide sequence of SEQ ID NO:1 or to the nucleotide sequence of the DNA insert of the plasmid deposited with ATCC as Accession Number 98375. Preferably, the isolated nucleic acid molecule corresponds to a naturally-occurring nucleic acid molecule. More preferably, the isolated nucleic acid encodes naturally-occurring human EMI1 or a biologically active portion thereof. Moreover, given the disclosure herein of an EMI1-encoding cDNA sequence (e.g., SEQ ID NO:1), antisense nucleic acid molecules (i.e., molecules which are complementary to the coding strand of the EMI1 cDNA sequence) are also provided by the invention.

Another aspect of the invention pertains to vectors, e.g., recombinant expression vectors, containing the nucleic acid molecules of the invention and host cells into which such vectors have been introduced. In one embodiment, such a host cell is used to produce EMI1 protein by culturing the host cell in a suitable medium. If desired, the EMI1 protein can be then isolated from the medium or the host cell.

Yet another aspect of the invention pertains to transgenic nonhuman animals in which an EMI1 gene has been introduced or altered. In one embodiment, the genome of the nonhuman animal has been altered by introduction of a nucleic acid molecule of the invention encoding EMI1 as a transgene. In another embodiment, an endogenous EMI1 gene within the genome of the nonhuman animal has been altered, e.g., functionally disrupted, by homologous recombination.

Still another aspect of the invention pertains to an isolated EMI1 protein or a portion, e.g., a biologically active portion, thereof. In a preferred embodiment, the isolated EMI1 protein or portion thereof can modulate a TGF-β response in a TGF-β responsive cell. In another preferred embodiment, the isolated EMI1 protein or portion thereof is sufficiently homologous to an amino acid sequence of SEQ ID NO:2 such that the protein or portion thereof maintains the ability to modulate a TGF-β response in a TGF-β responsive cell.

In one embodiment, the biologically active portion of the EMI1 protein includes a domain or motif, preferably a domain or motif which has an EMI1 activity. The domain can be WW domain. If the active portion of the protein which comprises the WW domain is isolated or derived from a human, it is preferred that the WW domain be at least about 55%, preferably at least about 60–65%, even more preferably at least about 70–75%, and most preferably at least about 80–90% or more homologous to SEQ ID NO:4. If the active portion of the protein which comprises the WW domain is isolated or derived from an animal which is not a mammal, it is preferred that the WW domain be at least about 75%, preferably at least about 80–85%, and most preferably at least about 90–95% or more homologous to SEQ ID NO:4. Preferably, the biologically active portion of the EMI1 protein which includes a WW domain also has one of the following activities: 1) it can interact with (e.g., bind to) an MADR protein; 2) it can modulate the activity of an MADR protein; 3) it can interact with (e.g., bind to) a protein having a PY motif; 4) it can modulate the activity of a protein having a PY motif; and 5) it can modulate a TGF-β response in a TGF-β responsive cell (e.g., an epithelial cell or an endothelial cell) to, for example, beneficially affect the TGF-β responsive cell.

The invention also provides an isolated preparation of an EMI1 protein. In preferred embodiments, the EMI1 protein comprises the amino acid sequence of SEQ ID NO:2 or an amino acid sequence encoded by the nucleotide sequence of the DNA insert of the plasmid deposited with ATCC as Accession Number 98375. In another preferred embodiment, the invention pertains to an isolated full length protein which is substantially homologous to the entire amino acid sequence of SEQ ID NO:2 (encoded by the open reading frame shown in SEQ ID NO:3). In yet another embodiment, the protein is at least about 60–70%, preferably at least about 80–85%, and more preferably at least about 86, 88, 90%, and most preferably at least about 90–95% or more homologous to the entire amino acid sequence of SEQ ID NO:2. In other embodiments, the isolated EMI1 protein comprises an amino acid sequence which is at least about 60–70% or more homologous to the amino acid sequence of SEQ ID NO:2 and has an one or more of the following activities: 1) it can interact with (e.g., bind to) to an MADR protein; 2) it can modulate the activity of an MADR protein; 3) it can interact with (e.g., bind to) a protein having a PY motif; 4) it can modulate the activity of a protein having a PY motif; and 5) it can modulate a TGF-β response in a TGF-β responsive cell (e.g., an epithelial cell or an endothelial cell) to, for example, beneficially affect the TGF-β responsive cell. Alternatively, the isolated EMI1 protein can comprise an amino acid sequence which is encoded by a nucleotide sequence which hybridizes, e.g., hybridizes under stringent conditions, or is at least about 60–65%, preferably at least about 70–75%, more preferably at least about 80–85%, and even more preferably at least about 90–95% or more homologous to the nucleotide sequence of SEQ ID NO:1 or the nucleotide sequence of the DNA insert of the plasmid deposited with ATCC as Accession Number 98375. It is also preferred that the preferred forms of EMI1 also have one or more of the EMI1 activities described herein.

The EMI1 protein (or polypeptide) or a biologically active portion thereof can be operatively linked to a non-EMI1 polypeptide to form a fusion protein. In addition, the EMI1 protein or a biologically active portion thereof can be incorporated into a pharmaceutical composition comprising the protein and a pharmaceutically acceptable carrier.

The EMI1 protein of the invention, or portions or fragments thereof, can be used to prepare anti-EMI1 antibodies. Accordingly, the invention also provides an antigenic peptide of EMI1 which comprises at least 8 amino acid residues of the amino acid sequence shown in SEQ ID NO:2 and encompasses an epitope of EMI1 such that an antibody raised against the peptide forms a specific immune complex with EMI1. Preferably, the antigenic peptide comprises at least 10 amino acid residues, more preferably at least 15 amino acid residues, even more preferably at least 20 amino acid residues, and most preferably at least 30 amino acid residues. The invention further provides an antibody that specifically binds EMI1. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention pertains to methods for modulating a cell associated activity, e.g., proliferation or differentiation. Such methods include contacting the cell with an agent which modulates EMI1 protein activity or EMI1 nucleic acid expression such that a cell associated activity is altered relative to a cell associated activity (e.g., the same cell associated activity) of the cell in the absence of the agent. In a preferred embodiment, the cell is capable of responding to TGF-β through a signaling pathway involving an EMI1 protein (e.g., an epithelial cell or an endothelial cell). The agent which modulates EMI1 activity can be an agent which stimulates EMI1 protein activity or EMI1 nucleic acid expression. Examples of agents which stimulate EMI1 protein activity or EMI1 nucleic acid expression include small molecules, active EMI1 proteins, and nucleic acids encoding EMI1 that have been introduced into the cell. Examples of agents which inhibit EMI1 activity or expression include small molecules, antisense EMI1 nucleic acid molecules, and antibodies that specifically bind to EMI1. In a preferred embodiment, the cell is present within a subject and the agent is administered to the subject.

The present invention also pertains to methods for treating subjects having various disorders. For example, the invention pertains to methods for treating a subject having a disorder characterized by aberrant EMI1 protein activity or nucleic acid expression such as a cardiovascular disorder, e.g., atherosclerosis, or a proliferative disorder, e.g., a proliferative disorder characterized by uncontrolled proliferation of epithelial cells. These methods include administering to the subject an EMI1 modulator (e.g., a small molecule) such that treatment of the subject occurs.

In another embodiment, the invention pertains to methods for treating a subject having a cardiovascular disorder, e.g., atherosclerosis, or a proliferative disorder, e.g., a proliferative disorder characterized by uncontrolled proliferation of epithelial cells, comprising administering to the subject an EMI1 modulator such that treatment occurs.

In other embodiments, the invention pertains to methods for treating a subject having a cardiovascular disorder or a proliferative disorder comprising administering to the subject an EMI1 protein or portion thereof such that treatment occurs. Cardiovascular and proliferative disorders can also be treated according to the invention by administering to the subject having the disorder a nucleic acid encoding an EMI1 protein or portion thereof such that treatment occurs.

The invention also pertains to methods for detecting genetic lesions in a EMI1 gene, thereby determining if a subject with the lesioned gene is at risk for (or is predisposed to have) a disorder characterized by aberrant or abnormal EMI1 nucleic acid expression or EMI1 protein activity, e.g., a cardiovascular disorder or a proliferative disorder. In preferred embodiments, the methods include detecting, in a sample of cells from the subject, the presence or absence of a genetic lesion characterized by an alteration affecting the integrity of a gene encoding an EMI1 protein, or the misexpression of the EMI1 gene.

Another aspect of the invention pertains to methods for detecting the presence of EMI1 in a biological sample. In a preferred embodiment, the methods involve contacting a biological sample (e.g., an endothelial cell sample) with a compound or an agent capable of detecting EMI1 protein or EMI1 mRNA such that the presence of EMI1 is detected in the biological sample. The compound or agent can be, for example, a labeled or labelable nucleic acid probe capable of hybridizing to EMI1 mRNA or a labeled or labelable antibody capable of binding to EMI1 protein. The invention further provides methods for diagnosis of a subject with, for example, a cardiovascular disease or a proliferative disorder, based on detection of EMI1 protein or mRNA. In one embodiment, the method involves contacting a cell or tissue sample (e.g., an epithelial cell or an endothelial cell sample) from the subject with an agent capable of detecting EMI1 protein or mRNA, determining the amount of EMI1 protein or mRNA expressed in the cell or tissue sample, comparing the amount of EMI1 protein or mRNA expressed in the cell or tissue sample to a control sample and forming a diagnosis based on the amount of EMI1 protein or mRNA expressed in the cell or tissue sample as compared to the control sample. Preferably, the cell sample is an endothelial cell sample. Kits for detecting EMI1 in a biological sample are also within the scope of the invention.

Still another aspect of the invention pertains to methods, e.g., screening assays, for identifying a compound for treating a disorder characterized by aberrant EMI1 nucleic acid expression or protein activity, e.g., a cardiovascular disorder or a proliferative disorder. These methods typically include assaying the ability of the compound or agent to modulate the expression of the EMI1 gene or the activity of the EMI1 protein thereby identifying a compound for treating a disorder characterized by aberrant EMI1 nucleic acid expression or protein activity. In a preferred embodiment, the method involves contacting a biological sample, e.g., a cell or tissue sample, e.g., an endothelial cell sample, obtained from a subject having the disorder with the compound or agent, determining the amount of EMI1 protein expressed and/or measuring the activity of the EMI1 protein in the biological sample, comparing the amount of EMI1 protein expressed in the biological sample and/or the measurable EMI1 biological activity in the cell to that of a control sample. An alteration in the amount of EMI1 protein expression or EMI1 activity in the cell exposed to the compound or agent in comparison to the control is indicative of a modulation of EMI1 expression and/or EMI1 activity.

The invention also pertains to methods for identifying a compound or agent which interacts with (e.g., binds to) an EMI1 protein. These methods can include the steps of contacting the EMI1 protein with the compound or agent under conditions which allow binding of the compound to the EMI1 protein to form a complex and detecting the formation of a complex of the EMI1 protein and the compound in which the ability of the compound to bind to the EMI1 protein is indicated by the presence of the compound in the complex.

The invention further pertains to methods for identifying a compound or agent which modulates, e.g., stimulates or inhibits, the interaction of the EMI1 protein with a target molecule, e.g., MADR6, MADR7, or a complex of MADR6 and MADR7. In these methods, the EMI1 protein is contacted, in the presence of the compound or agent, with the target molecule under conditions which allow binding of the target molecule to the EMI1 protein to form a complex. An alteration, e.g., an increase or decrease, in complex formation between the EMI1 protein and the target molecule as compared to the amount of complex formed in the absence of the compound or agent is indicative of the ability of the compound or agent to modulate the interaction of the EMI1 protein with a target molecule.

BRIEF DESCRIPTION OF THE DRAWING

FIG. 1 depicts the EMI1 nucleotide (SEQ ID NO:1) and amino acid (SEQ ID NO:2) sequence.

DETAILED DESCRIPTION OF THE INVENTION

The present invention is based on the discovery of novel molecules, referred to herein as EMI1 nucleic acid and protein molecules, which play a role in or function in growth factor signaling pathways. In one embodiment, the EMI1 molecules modulate the activity of one or more proteins involved in a growth factor signaling pathway, e.g., a TGF-β3 signaling pathway. In a preferred embodiment, the EMI1 molecules of the present invention are capable of modulating the activity of proteins involved in the TGF-β signaling pathway to thereby modulate the effects of TGF-β3 on TGF-β responsive cells. In a particularly preferred embodiment, the EMI1 molecules are capable of modulating the activity of MADR proteins, such as MADR6 (the fchd534 gene product) and MADR7 (the fchd540 gene product), in TGF-β responsive cells. As used herein, an "MADR protein" is a protein which is involved in the TGF-β signaling pathway and 1) which includes a domain of at least about 10 amino acid residues which is at least about 40% or more homologous to a domain of the Drosophila MAD protein; or 2) which includes a PY domain (as defined herein). Examples of human MADR proteins include hMAD2-4, MADR1, MADR2, MADR6, and MADR7. Non-human MADR proteins include, for example, Sma2-4 (from C. elegans), Mad2 (from Xenopus), and Drosophila MAD. Using Northern analysis, MADR6 has been found to be expressed in the following tissues: heart, placenta, lung, prostate, ovary, and small intestine; and MADR7 has been found to be expressed in the following tissues: heart, brain, placenta, lung, liver, skeletal muscle, kidney, pancreas, spleen, thymus, prostate, testis, ovary, small intestine, colon, and peripheral blood leukocytes. As MADR proteins, e.g., MADR6 and MADR7, are involved in the TGF-β signaling pathway in TGF-β responsive cells and the EMI1 molecules of the invention modulate MADR activity, the EMI1 molecules can modulate a cell's response to TGF-β. For example, MADR6 and MADR7 inhibit the beneficial effects (e.g., vascular injury reparatory effects) (Border et al. (1995) Nature Medicine 1:1000; Grainger et al. (1995) Nature Medicine 1:1067–1073; Nikol et al. (1992) J. Clin. Invest. 90:1582–1592; Kojima et al. (1991) J. Cell Biol. 113:1439–1445)) of TGF-β on endothelial cells. Thus, the EMI1 protein, by interacting with (e.g., binding to) MADR6 and/or MADR7, can modulate (e.g., inhibit) the TGF-β inhibitory effects of MADR6 and MADR7 in endothelial cells to thereby allow the cells to more readily receive the beneficial effects of TGF-β. Thus, EMI1 molecules (or modulators thereof) of the present invention can be used to treat various cardiovascular disorders such as atherosclerosis, ischemia/reperfusion, hypertension, restenosis, and arterial inflammation.

In another embodiment, the EMI1 molecules of the invention are capable of modulating the activity of an MADR protein, such as MADR1, in epithelial cells. For example, MADR1 mediates TGF-β tumor suppressor effects in epithelial cells, e.g., gut-derived epithelial cells. Thus, the EMI1 protein, by interacting with (e.g., binding to) MADR1, can modulate (e.g., stimulate or inhibit) the TGF-β tumor suppressor effects of MADR1 in epithelial cells such as colorectal carcinoma cells to thereby inhibit further growth of the cells, e.g., render the cells more responsive to the tumor suppressor effects of TGF-β. Thus, EMI1 molecules (or modulators thereof) of the present invention can also be used to treat various proliferative disorders, e.g., cancers, such as epithelial cell (e.g., gut associated or gut derived epithelial cell) cancers. In addition, as the EMI1 molecules of the present invention can modulate a TGF-β response in a TGF-β responsive cell such as an endothelial cell, the EMI1 molecules (or modulators thereof) can be used to modulate angiogenesis, e.g., pathological angiogenesis (e.g., tumor angiogenesis) and thus to treat disorders characterized by or associated with pathological angiogenesis.

TGF-β is also capable of initiating various effects in a variety of different cell types. For example, TGF-β is an immune regulatory molecule which can act to both activate and suppress actions of leukocytes, T cells, and macrophages. Furthermore, administration of TGF-β in animal models of autoimmune diseases has been shown to ameliorate autoimmune diseases including experimental autoimmune encephalitis (a model of multiple sclerosis) and experimental arthiritis. Thus, molecules, such as the EMI1 molecules (or modulators thereof) described herein, which are capable of modulating a TGF-β in a TGF-β responsive cell, can also modulate TGI-p responses in immune cells and thus be used to treat autoimmune diseases. In another example, TGF-β is known to act on connective tissue cells to modulate the production of extracellular matrix molecules. Overproduction of extracellular matrix molecules results in fibrotic disorders which can affect vital organs such as the kidney, liver, lung, and heart. Thus, modulation of TGF-β activity in connective tissue cells, by, for example, modulating EMI1 activity, is another approach to treating connective tissue disorders, e.g., fibrotic disorders.

In addition, abnormal production of TGF-β has been implicated in altered wound healing processes. For example, underproduction of TGF-β has been linked to impaired wound healing in some subjects, e.g., elderly subjects, subjects with diabetes. Thus, modulation of TGF-β activity in cells involved in wound healing, e.g., connective tissue cells by, for example, modulating EMI1 activity, is one approach to modulating wound healing.

EMI1 nucleic acid molecules were identified from human breast tissue based on their ability, as determined using yeast two-hybrid assays (described in detail in Example 1), to interact with human MADR6 and MADR7 proteins. As described above, the human MADR6 and MADR7 proteins were previously identified based on their differential expression in an experimental paradigm of cardiovascular disease. See U.S. Ser. No. 08/599,654, filed Feb. 9, 1996, and U.S. Ser. No. 08/799,910, filed Feb. 13, 1997, the contents of which are expressly incorporated herein by reference. A plasmid containing the full length nucleotide sequence encoding MADR6 was deposited with the Agricultural Research Service Culture Collection (NRRL), Peoria, Ill., on Jun. 6, 1995 and assigned Accession Number B-21459. A plasmid containing the full length nucleotide sequence encoding MADR7 was deposited with the American Type Culture Collection (ATCC), Rockville, Md., on Feb. 7, 1996 and assigned Accession Number 69984.

Because of its ability to interact with (e.g., bind to) the MADR6 and MADR7 proteins (and MADR proteins described in the Examples below) which are proteins involved in the TGF-β signaling pathway, the EMI1 protein is also a protein which functions in the TGF-β signaling pathway.

The nucleotide sequence of the isolated human EMI1 cDNA and the predicted amino acid sequence of the human EMI1 protein are shown in FIG. 1 and in SEQ ID NOs:1 and 2, respectively. A plasmid containing the full length nucleotide sequence encoding human EMI1 (with the DNA insert name of EpFWA 11) was deposited with ATCC on Mar. 27,1997 and assigned Accession Number 98375. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

A GenBank™ search using the EMI1 nucleotide sequence of SEQ ID NO:1 revealed four ESTs, one human and three mouse, which were similar to different regions of the nucleotide sequence of SEQ ID NO:1. The human EST, ZC51D02 (Accession Number AA037190), is identical to a portion (nucleotides 1262 to 1290) of the 3' untranslated sequence of SEQ ID NO:1. The first mouse EST, MJ40E12.R1 (Accession Number AA051144), is approximately 88% homologous to nucleotides 39 to 529 of SEQ ID NO:1. The second mouse EST, ME30A06.R1 (Accession Number W66992), is approximately 88% homologous to nucleotides 58 to 416 of SEQ ID NO:1. The third mouse EST, MA09E05.R1 (Accession Number W54933), is approximately 88% homologous to nucleotides 25 to 275 of SEQ ID NO:1. As no reading frame can be determined from an EST (such as the an EST identified in the above database searches), an amino acid sequence encoded by the EST cannot be determined.

GenPept™ and SwissProt™ database searches of the EMI1 amino acid sequence of SEQ ID NO:2 revealed three polypeptide sequences which include WW domains which are similar to SEQ ID NO:4. Two of these polypeptide sequences are derived from yeast and one of the polypeptide sequences is derived from humans. The first yeast polypeptide sequence, RSP5 (SwissProt™ Accession Number P39940), includes a domain which is approximately 70% homologous to SEQ ID NO:4. The second yeast polypeptide sequence, ubiquitin protein ligase (Genpept™ Accession Number Y07592), includes a domain which is approximately 63% homologous to SEQ ID NO:4. The human polypeptide sequence, NEDD4 (SwissProt™ Accession Number T46934) includes a domain which is approximately 53% homologous to SEQ ID NO:4. GenPept™ and SwissProt™ database searches of the amino acid sequence of SEQ ID NO:2 (using a score of 50 and a word length of 3) revealed no full length human protein sequence. Thus, the present invention also pertains to proteins which have an amino acid sequence which is substantially homologous to the amino acid sequence of SEQ ID NO:2 (encoded by the open reading frame shown in SEQ ID NO:3) or an amino acid sequence encoded by the nucleotide sequence of the DNA insert of the plasmid deposited with ATCC as Accession Number 98375. As used herein, a protein which has an amino acid sequence which is substantially homologous to a selected amino acid sequence is least about 50% homologous to the selected amino acid sequence, e.g., the entire selected amino acid sequence. A protein which has an amino acid sequence which is substantially homologous to a selected amino acid sequence can also be least about 60–70%, preferably at least about 80–85%, and more preferably at least about 86, 88, 90%, and most preferably at least about 90–95% or more homologous to selected amino acid sequence.

The human EMI1 gene, which is approximately 1290 nucleotides in length, encodes a full length protein having a molecular weight of approximately 21 kD and which is approximately 335 amino acid residues in length. The EMI1 protein is expressed at least in endothelial cells and, as the nucleic acid encoding EMI1 protein was isolated from a human breast library, EMI1 protein is also most likely expressed in cells, e.g., parenchymal cells (e.g., epithelial cells) and stromal (e.g., connective tissue cells) cells, found in breast tissue. The carboxy-terminal 36 amino acid residues (amino acid residues 300 to 335) comprise a WW domain (SEQ ID NO:4). As used herein, the term "WW domain" refers to a structural amino acid motif which includes about 30–40 (typically 38) semiconserved amino acid residues two of which are conserved tryptophan (W) residues. A WW domain also preferably includes a high content of polar amino acid residues and the presence of prolines distributed preferentially towards both termini of the protein sequence (Sudol et al. (1995) *FEBS Letters* 369:67–71). The WW domain of EMI1 comprises amino acids 300 to 335 of SEQ ID NO:2 (shown as SEQ ID NO:4) (which is encoded by nucleotides 974 to 1081 of SEQ ID NO:1) as follows (the proline and conserved tryptophan residues are in bold and underlined):

300    DALPAGWEQRELPNGRVYYVDHNTKTTTWER
       PLPPG 335 (SEQ ID NO:4)

The consensus sequence bound by the WW domain of the EMI1 protein comprises a PY motif (Chen and Sudol (1995) *PNAS* 92:7819–7823). As used herein, "a PY motif or PY domain" is an amino acid sequence of at least about 4–5 amino acid residues which includes a proline-rich domain followed by a tyrosine residue. The particular PY motifs to which the WW domain of the EMI1 protein bind include the following amino acid sequence: XPPXY (SEQ ID NO:16) wherein X can be any amino acid residue. Several MADR proteins, including, for example, MADR1, hMAD2–4, MADR6, MADR7, contain a PY motif. The PY motifs of several MADR proteins are set forth in Example 4 (Table 5) below.

The EMI1 protein or a biologically active portion or fragment of the invention can have one or more of the following activities: 1) it can interact with (e.g., bind to) an MADR protein; 2) it can modulate the activity of an MADR protein; 3) it can interact with (e.g., bind to) a protein having a PY motif, 4) it can modulate the activity of a protein having a PY motif; and 5) it can modulate a TGF-β response in a TGF-β responsive cell, e.g., an epithelial cell, an endothelial cell, to thereby beneficially affect the TGF-β responsive cell.

Various aspects of the invention are described in further detail in the following subsections:

I. Isolated Nucleic Acid Molecules

One aspect of the invention pertains to isolated nucleic acid molecules that encode EMI1 or biologically active portions thereof, as well as nucleic acid fragments sufficient for use as hybridization probes to identify EMI1 -encoding nucleic acid (e.g., EMI1 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated EMI1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an endothelial cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1, or a portion thereof, can be isolated using standard molecular biology techniques and the sequence information provided herein. For example, a human EMI1 cDNA can be isolated from a human breast library using all or portion of SEQ ID NO:1 as a hybridization probe and standard hybridization techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NO:1 can be isolated by the polymerase chain reaction using oligonucleotide primers designed based upon the sequence of SEQ ID NO:1. For example, mRNA can be isolated from normal endothelial cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a EMI1 nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1 or the nucleotide sequence of the DNA insert of the plasmid deposited with ATCC as Accession Number 98375. The sequence of SEQ ID NO:1 corresponds to the human EMI1 cDNA. This cDNA comprises sequences encoding the EMI1 protein (i.e., "the coding region", from nucleotides 77 to 1081), as well as 5' untranslated sequences (nucleotides 1 to 76) and 3' untranslated sequences (nucleotides 1082 to 1290). Alternatively, the nucleic acid molecule can comprise only the coding region of SEQ ID NO:1 (e.g., nucleotides 77 to 1081).

In another preferred embodiment, an isolated nucleic acid molecule of the invention comprises a nucleic acid molecule which is a complement of the nucleotide sequence shown in SEQ ID NO:1, the nucleotide sequence of the DNA insert of the plasmid deposited with ATCC as Accession Number 98375, or a portion of either of these nucleotide sequences. A nucleic acid molecule which is complementary to the nucleotide sequence shown in SEQ ID NO:1 is one which is sufficiently complementary to the nucleotide sequence shown in SEQ ID NO:1 such that it can hybridize to the nucleotide sequence shown in SEQ ID NO:1, thereby forming a stable duplex.

In still another preferred embodiment, an isolated nucleic acid molecule of the invention comprises a nucleotide sequence which is at least about 60–65%, preferably at least about 70–75%, more preferably at least about 80–85%, and even more preferably at least about 90–95% or more homologous to the nucleotide sequence shown in SEQ ID NO:1, the nucleotide sequence of the DNA insert of the plasmid deposited with ATCC as Accession Number 98375, or a portion of either of these nucleotide sequences. In an additional preferred embodiment, an isolated nucleic acid molecule of the invention comprises a nucleotide sequence which hybridizes, e.g., hybridizes under stringent conditions, to the nucleotide sequence shown in SEQ ID NO:1, the nucleotide sequence of the DNA insert of the plasmid deposited with ATCC as Accession Number 98375, or a portion of either of these nucleotide sequences.

Moreover, the nucleic acid molecule of the invention can comprise only a portion of the coding region of SEQ ID NO:1, for example a fragment which can be used as a probe or primer or a fragment encoding a biologically active portion of EMI1. The nucleotide sequence determined from the cloning of the EMI1 gene from a mammal allows for the generation of probes and primers designed for use in identifying and/or cloning EMI1 homologues in other cell types, e.g. from other tissues, as well as EMI1 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO: I sense, an anti-sense sequence of SEQ ID NO:1, or naturally occurring mutants thereof. Primers based on the nucleotide sequence in SEQ ID NO:1 can be used in PCR reactions to clone EMI1 homologues. Probes based on the EMI1 nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress an EMI1 protein, such as by measuring a level of an EMI1 -encoding nucleic acid in a sample of cells from a subject e.g., detecting EMI1 mRNA levels or determining whether a genomic EMI1 gene has been mutated or deleted.

In one embodiment, the nucleic acid molecule of the invention encodes a protein or portion thereof which includes an amino acid sequence which is sufficiently homologous to an amino acid sequence of SEQ ID NO:2 or an amino acid sequence encoded by the nucleotide sequence of the DNA insert of the plasmid deposited with ATCC as Accession Number 98375 such that the protein or portion thereof maintains the ability to modulate a TGF-β response in a TGF-β responsive cell. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2) amino acid residues to an amino acid sequence of SEQ ID NO:2 or an amino acid sequence encoded by the nucleotide sequence of the DNA insert of the plasmid deposited with ATCC as Accession Number 98375 such that the protein or portion thereof is able to modulate a TGF-β response in a TGF-β responsive cell. Members of the TGF-β family of proteins, as described herein, initiate a variety of responses in many different cells types. Examples of such responses are also described herein. Thus, a "TGF-β response in a TGF-β responsive cell" is a cellular response to a member of the TGF-β family of proteins. Non-limiting examples of the subfamilies included in the TGF-β family of proteins include members of the TGF-β subfamily, which comprises at least four genes that are much more similar to TGF-β than to other members of the TGFβ family of proteins; the activin subfamily, comprising homo- or heterodimers or two sub-units, inhibinβ-A and inhibinβ-B; the decapentaplegic (DPP) subfamily, including the mammalian factors BMP2 and BMP4, which can induce the formation of ectopic bone and cartilage when implanted under the skin or into muscles; and the 60A subfamily, which includes a number of mammalian homologues, e.g., BMP5–8, with osteoinductive activity. Other members of the TGFβ family of proteins include growth differentiation factor 1 (GDF-1), GDF-3/VGR-2, dorsalin, nodal, mullerian-inhibiting substance (MIS), and glial-derived neurotrophic growth factor (GDNF). The DPP and 60A subfamilies are related more closely to one another than to other members of the TGFβ superfamily, and have often been grouped together as part of a larger collection of molecules called DVR (dpp and vg1 related). In another embodiment, the protein is at least about 60–70%, preferably at least about 80–85%, and more preferably at least about 86, 88, 90%, and most preferably at least about 90–95% or more homologous to the entire amino acid sequence of SEQ ID NO:2.

Portions of proteins encoded by the EMI1 nucleic acid molecule of the invention are preferably biologically active portions of the EMI1 protein. As used herein, the term "biologically active portion of EMI1 " is intended to include a portion, e.g., a domain/motif, of EMI1 that has one or more of the following activities: 1) it can interact with (e.g., bind to) an MADR protein; 2) it can modulate the activity of an MADR protein; 3) it can interact with (e.g., bind to) a protein having a PY motif; 4) it can modulate the activity of a protein having a PY motif; and 5) it can modulate a TGF-β response in a TGF-β responsive cell, e.g., an epithelial cell, an endothelial cell, to, for example, beneficially affect the TGF-β responsive cell. Standard binding assays, e.g., immu-noprecipitations and yeast two-hybrid assays as described herein, can be performed to determine the ability of an EMI1 protein or a biologically active portion thereof to interact with (e.g., bind to) an MADR protein or a protein having a PY motif. To determine whether an EMI1 protein or a biologically active portion thereof can modulate TGF-β response in a TGF-β responsive cell such as an endothelial cell, endothelial cells e.g., bovine aortic endothelial cells, can be transfected with a TGF-β responsive reporter construct, e.g., p3TP-Lux (Wrana et al. (1994) *Nature* 370:341–347) which responds to TGF-β signaling by expressing luciferase, and a nucleic acid encoding the EMI1 protein or biologically active portion thereof. The endothelial cells can then be exposed to TGF-β. After exposure of the cells to TGF-β, the cells can be harvested and lysed and reporter activity, e.g., luciferase activity, can be measured and compared to control reporter activity. The ability of an EMI1 protein or a biologically active portion thereof to modulate an MADR protein activity can be determined using an assay similar to the assay described above for determining the ability of an EMI1 protein or a biologically active portion thereof to modulate TGF-β response in TGF-β responsive cells. In particular, endothelial cells, e.g., bovine aortic endothelial cells, can be transfected with a TGF-β responsive reporter construct, e.g., p3TP-Lux (Wrana et al. (1994) *Nature* 370:341–347) which responds to TGF-β signaling by expressing luciferase, and an expression vector which expresses an MADR protein (e.g., pCI expression vectors (Promega, Madison, Wis.) which express MADR6 and/or MADR7), PCMV5MADR1-Flag (Hoodless et al. (1996) *Cell* 85:489–500), or PCMV5MADR2-Flag (Eppert et al. (1996) *Cell* 86:543–552). The endothelial cells can then be exposed to TGF-β. After exposure of the cells to TGF-β, the cells can be harvested and lysed and reporter activity, e.g., luciferase activity, can be measured and compared to reporter activity in endothelial cells which also include nucleic acid encoding the EMI1 protein or biologically active portion thereof. An alteration in reporter activity in the endothelial cells which include nucleic acid encoding the EMI1 protein as compared to reporter activity in the endothelial cells without nucleic acid encoding the EMI1 protein is indicative of a modulation of a TGF-β response in the TGF-β responsive cell.

In one embodiment, the biologically active portion of EMI1 comprises a WW domain. Preferably, the WW domain is encoded by a nucleic acid molecule derived from a human and is at least about 55%, preferably at least about 60–65%, even more preferably at least about 70–75%, and most preferably at least about 80–90% or more homologous to SEQ ID NO:4. If the WW domain is encoded by a non-mammalian nucleic acid, it is preferably at least about 75%, preferably at least about 80–85%, most preferably at least about 90–95% or more homologous to SEQ ID NO:4. In a preferred embodiment, the biologically active portion of the protein which includes the WW domain can modulate the activity of a protein having a PY motif and/or modulate a TGF-β response in a TGF-β responsive cell, e.g., an endothelial cell, to thereby beneficially affect the TGF-β responsive cell. In a preferred embodiment, the biologically active portion comprises the WW domain of EMI1 as represented by amino acid residues 300 to 335 of SEQ ID NO:2 and as SEQ ID NO:4. Additional nucleic acid fragments encoding biologically active portions of EMI1 can be prepared by isolating a portion of SEQ ID NO:1, expressing the encoded portion of EMI1 protein or peptide (e.g., by recombinant expression in vitro) and assessing the activity of the encoded portion of EMI1 protein or peptide.

The invention further encompasses nucleic acid molecules that differ from the nucleotide sequence shown in SEQ ID NO:1 (and portions thereof) due to degeneracy of the genetic code and thus encode the same EMI1 protein as that encoded by the nucleotide sequence shown in SEQ ID NO:1. In another embodiment, an isolated nucleic acid molecule of the invention has a nucleotide sequence encoding a protein having an amino acid sequence shown in SEQ ID NO:2 or a protein having an amino acid sequence encoded by the nucleotide sequence of the DNA insert of the plasmid deposited with ATCC as Accession Number 98375. In a still further embodiment, the nucleic acid molecule of the invention encodes a full length human protein which is substantially homologous to the amino acid sequence of SEQ ID NO:2 (encoded by the open reading frame shown in SEQ ID NO:3) or an amino acid sequence encoded by the nucleotide sequence of the DNA insert of the plasmid deposited with ATCC as Accession Number 98375.

In addition to the human EMI1 nucleotide sequence shown in SEQ ID NO:1, it will be appreciated by those skilled in the art that DNA sequence polymorphisms that lead to changes in the amino acid sequences of EMI1 may exist within a population (e.g., the human population). Such genetic polymorphism in the EMI1 gene may exist among individuals within a population due to natural allelic variation. As used herein, the terms "gene" and "recombinant gene" refer to nucleic acid molecules comprising an open reading frame encoding an EMI1 protein, preferably a mammalian EMI1 protein. Such natural allelic variations can typically result in 1–5% variance in the nucleotide sequence of the EMI1 gene. Any and all such nucleotide variations and resulting amino acid polymorphisms in EMI1 that are the result of natural allelic variation and that do not alter the functional activity of EMI1 are intended to be within the scope of the invention. Moreover, nucleic acid molecules encoding EMI1 proteins from other species, and thus which have a nucleotide sequence which differs from the human sequence of SEQ ID NO:1, are intended to be within the scope of the invention. Nucleic acid molecules corresponding to natural allelic variants and nonhuman homologues of the human EMI1 cDNA of the invention can be isolated based on their homology to the human EMI1 nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1 or the nucleotide sequence of the DNA insert of the plasmid deposited with ATCC as Accession Number 98375. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human EMI1.

In addition to naturally-occurring allelic variants of the EMI1 sequence that may exist in the population, the skilled artisan will further appreciate that changes can be introduced by mutation into the nucleotide sequence of SEQ ID NO:1, thereby leading to changes in the amino acid sequence of the encoded EMI1 protein, without altering the functional ability of the EMI1 protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of EMI1 (e.g., the sequence of SEQ ID NO:2) without altering the activity of EMI1, whereas an "essential" amino acid residue is required for EMI1 activity. For example, conserved amino acid residues, e.g., tryptophans and prolines, in the WW domain of EMI1 are most likely important for binding to MADR proteins and are thus essential residues of EMI1. Other amino acid residues, however, (e.g., those that are not conserved or only semi-conserved in the WW domain) may not be essential for activity and thus are likely to be amenable to alteration without altering EMI1 activity.

Accordingly, another aspect of the invention pertains to nucleic acid molecules encoding EMI1 proteins that contain changes in amino acid residues that are not essential for EMI1 activity. Such EMI1 proteins differ in amino acid sequence from SEQ ID NO:2 yet retain at least one of the EMI1 activities described herein. In one embodiment, the isolated nucleic acid molecule comprises a nucleotide sequence encoding a protein, wherein the protein comprises an amino acid sequence at least about 60% homologous to the amino acid sequence of SEQ ID NO:2 and is capable of modulating a TGF-β response in a TGF-β responsive cell. Preferably, the protein encoded by the nucleic acid molecule is at least about 70% homologous to SEQ ID NO:2, more preferably at least about 80–85% homologous to SEQ ID NO:2, even more preferably at least about 90% homologous to SEQ ID NO:2, and most preferably at least about 95–99% homologous to SEQ ID NO:2.

To determine the percent homology of two amino acid sequences (e.g., SEQ ID NO:2 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence (e.g., a mutant form of EMI1), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding an EMI1 protein homologous to the protein of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in EMI1 is preferably replaced with another amino acid residue from the same side chain family. Alternatively, in another embodiment, mutations can be introduced randomly along all or part of an EMI1 coding sequence, such as by saturation mutagenesis, and the resultant mutants can be screened for an EMI1 activity described herein to identify mutants that retain EMI1 activity. Following mutagenesis of SEQ ID NO:1, the encoded protein can be expressed recombinantly (e.g., as described in Examples 2 and 3) and the activity of the protein can be determined using, for example, assays described herein.

In addition to the nucleic acid molecules encoding EMI1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire EMI1 coding strand, or to only a portion thereof. In one embodiment, an antisense nucleic acid molecule is antisense to a "coding region" of the coding strand of a nucleotide sequence encoding EMI1. The term "coding region" refers to the region of the nucleotide sequence comprising codons which are translated into amino acid residues (e.g., the entire coding region of SEQ ID NO:1 comprises nucleotides 77 to 1081). In another embodiment, the antisense nucleic acid molecule is antisense to a "noncoding region" of the coding strand of a nucleotide sequence encoding EMI1. The term "noncoding region" refers to 5' and 3' sequences which flank the coding region that are not translated into amino acids (i.e., also referred to as 5' and 3' untranslated regions).

Given the coding strand sequences encoding EMI1 disclosed herein (e.g., SEQ ID NO:1), antisense nucleic acids of the invention can be designed according to the rules of Watson and Crick base pairing. The antisense nucleic acid molecule can be complementary to the entire coding region of EMI1 mRNA, but more preferably is an oligonucleotide which is antisense to only a portion of the coding or noncoding region of EMI1 mRNA. For example, the antisense oligonucleotide can be complementary to the region surrounding the translation start site of EMI1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an EMI1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave EMI1 mRNA transcripts to thereby inhibit translation of EMI1 mRNA. A ribozyme having specificity for an EMI1 -encoding nucleic acid can be designed based upon the nucleotide sequence of an EMI1 cDNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in an EMI1-encoding mRNA. See, e.g., Cech et al. U.S. Pat. No. 4,987,071 and Cech et al. U.S. Pat. No. 5,116,742. Alternatively, EMI1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, EMI1 gene expression can be inhibited by targeting nucleotide sequences complementary to the regulatory region of the EMI1 (e.g., the EMI1 promoter and/or enhancers) to form triple helical structures that prevent transcription of the EMI1 gene in target cells. See generally, Helene, C. (1991) *Anticancer Drug Des.* 6(6):56984; Helene, C. et al. (1992) *Ann. N.Y. Acad. Sci.* 660:27–36; and Maher, L. J. (1992) *Bioassays* 14(12):807–15.

II. Recombinant Expression Vectors and Host Cells

Another aspect of the invention pertains to vectors, preferably expression vectors, containing a nucleic acid encoding EMI1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" C. an be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology. Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., EMI1 proteins, mutant forms of EMI1, fusion proteins, etc.).

The recombinant expression vectors of the invention can be designed for expression of EMI1 in prokaryotic or eukaryotic cells. For example, EMI1 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the EMI1 is cloned into a pGEX expression vector to create a vector encoding a fusion protein comprising, from the N-terminus to the C-terminus, GST-thrombin cleavage site-EMI1. The fusion protein can be purified by affinity chromatography using glutathione-agarose resin. Recombinant EMI1 unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the EMI1 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, EMI1 can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3 :537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to EMI1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, EMI1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning. A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding EMI1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) EMI1 protein. Accordingly, the invention further provides methods for producing EMI1 protein using the host cells of the invention. In one embodiment, the method comprises culturing the host cell of invention (into which a recombinant expression vector encoding EMI1 has been introduced) in a suitable medium until EMI1 is produced. In another embodiment, the method further comprises isolating EMI1 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as cardiovascular disorders and proliferative disorders. For example, in one embodiment, a host cell of the invention is a fertilized oocyte or an embryonic stem cell into which EMI1 -coding sequences have been introduced. Such host cells can then be used to create non-human transgenic animals in which exogenous EMI1 sequences have been introduced into their genome or homologous recombinant animals in which endogenous EMI1 sequences have been altered. Such animals are useful for studying the function and/or activity of EMI1 and for identifying and/or evaluating modulators of EMI1 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous EMI1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing EMI1-encoding nucleic acid into the male pronuclei of a fertilized oocyte, e.g., by microinjection, retroviral infection, and allowing the oocyte to develop in a pseudopregnant female foster animal. The human EMI1 cDNA sequence of SEQ ID NO:1 can be introduced as a transgene into the genome of a nonhuman animal. Alternatively, a nonhuman homologue of the human EMI1 gene, such as a mouse EMI 1 gene, can be isolated based on hybridization to the human EMI1 cDNA (described further in subsection I above) and used as a transgene. Intronic sequences and polyadenylation signals can also be included in the transgene to increase the efficiency of expression of the transgene. A tissue-specific regulatory sequence(s) can be operably linked to the EMI1 transgene to direct expression of EMI1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Fmbryo*, (Cold Spring Harbor Laboratory Press, Cold Spring Harbor, N.Y., 1986). Similar methods are used for production of other transgenic animals. A transgenic founder animal can be identified based upon the presence of the EMI1 transgene in its genome and/or expression of EMI1 mRNA in tissues or cells of the animals. A transgenic founder animal can then be used to breed additional animals carrying the transgene. Moreover, transgenic animals carrying a transgene encoding EMI1 can further be bred to other transgenic animals carrying other transgenes.

To create a homologous recombinant animal, a vector is prepared which contains at least a portion of an EMI1 gene into which a deletion, addition or substitution has been introduced to thereby alter, e.g., functionally disrupt, the EMI1 gene. The EMI1 gene can be a human gene (e.g., from a human genomic clone isolated from a human genomic library screened with the cDNA of SEQ ID NO:1), but more preferably, is a nonhuman homologue of a human EMI1 gene. For example, a mouse EMI1 gene can be isolated from a mouse genomic DNA library using the human EMI1 cDNA of SEQ ID NO:1 as a probe. The mouse EMI1 gene then can be used to construct a homologous recombination vector suitable for altering an endogenous EMI1 gene in the mouse genome. In a preferred embodiment, the vector is designed such that, upon homologous recombination, the endogenous EMI1 gene is functionally disrupted (i.e., no longer encodes a functional protein; also referred to as a "knock out" vector). Alternatively, the vector can be designed such that, upon homologous recombination, the endogenous EMI1 gene is mutated or otherwise altered but still encodes functional protein (e.g., the upstream regulatory region can be altered to thereby alter the expression of the endogenous EMI1 protein). In the homologous recombination vector, the altered portion of the EMI1 gene is flanked at its 5' and 3' ends by additional nucleic acid of the EMI1 gene to allow for homologous recombination to occur between the exogenous EMI1 gene carried by the vector and an endogenous EMI1 gene in an embryonic stem cell. The additional flanking EMI1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced EMI1 gene has homologously recombined with the endogenous EMI1 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhumans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated EMI1 Proteins and Anti-EMI1 Antibodies

Another aspect of the invention pertains to isolated EMI1 proteins, and biologically active portions thereof, as well as peptide fragments suitable for use as immunogens to raise anti-EMI1 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of EMI1 protein in which the protein is separated from cellular components of the cells in which it is naturally or recombinantly produced. In one embodiment, the language "substantially free of cellular material" includes preparations of EMI1 protein having less than about 30% (by dry weight) of non-EMI1 protein (also referred to herein as a "contaminating protein"), more preferably less than about 20% of non-EMI1 protein, still more preferably less than about 10% of non-EMI1 protein, and most preferably less than about 5% non-EMI1 protein. When the EMI1 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of EMI1 protein in which the protein is separated from chemical precursors or other chemicals which are involved in the synthesis of the protein. In one embodiment, the language "substantially free of chemical precursors or other chemicals" includes preparations of EMI1 protein having less than about 30% (by dry weight) of chemical precursors or non-EMI1 chemicals, more preferably less than about 20% chemical precursors or non-EMI1 chemicals, still more preferably less than about 10% chemical precursors or non-EMI1 chemicals, and most preferably less than about 5% chemical precursors or non-EMI1 chemicals. In preferred embodiments, isolated proteins or biologically active portions thereof lack contaminating proteins from the same animal from which the EMI1 protein is derived. Typically, such proteins are produced by recombinant expression of, for example, a human EMI1 protein in a nonhuman cell.

An isolated EMI1 protein or a portion thereof of the invention can modulate a TGF-β response in a TGF-β responsive cell. In preferred embodiments, the protein or portion thereof comprises an amino acid sequence which is sufficiently homologous to an amino acid sequence of SEQ ID NO:2 such that the protein or portion thereof maintains the ability to modulate a TGF-β response in a TGF-β responsive cell. The portion of the protein is preferably a biologically active portion as described herein. In another preferred embodiment, the EMI1 protein (i.e., amino acid residues 1–335) has an amino acid sequence shown in SEQ ID NO:2 or an amino acid sequence which is encoded by the nucleotide sequence of the DNA insert of the plasmid deposited with ATCC as Accession Number 98375. In yet another preferred embodiment, the EMI1 protein has an amino acid sequence which is encoded by a nucleotide sequence which hybridizes, e.g., hybridizes under stringent conditions, to the nucleotide sequence of the DNA insert of the plasmid deposited with ATCC as Accession Number 98375. In still another preferred embodiment, the EMI1 protein has an amino acid sequence which is encoded by a nucleotide sequence that is at least about 60–65%, preferably at least about 70–75%, more preferably at least about 80–85%, and even more preferably at least about 90–95% or more homologous to the nucleotide sequence of the DNA insert of the plasmid deposited with ATCC as Accession Number 98375. The preferred EMI1 proteins of the present invention also preferably possess at least one of the EMI1 activities described herein. For example, a preferred EMI1 protein of the present invention includes an amino acid sequence encoded by a nucleotide sequence which hybridizes, e.g., hybridizes under stringent conditions, to the nucleotide sequence of the DNA insert of the plasmid deposited with ATCC as Accession Number 98375 and which can modulate a TGF-β response in a TGF-β responsive cell.

In other embodiments, the EMI1 protein is substantially homologous to the amino acid sequence of SEQ ID NO:2 and retains the functional activity of the protein of SEQ ID NO:2 yet differs in amino acid sequence due to natural allelic variation or mutagenesis, as described in detail in subsection I above. Accordingly, in another embodiment, the EMI1 protein is a protein which comprises an amino acid sequence which is at least about 60–70%, preferably at least about 80–85%, and more preferably at least about 86, 88, 90%, and most preferably at least about 90–95% or more homologous to the entire amino acid sequence of SEQ ID NO:2 and which has at least one of the EMI1 activities described herein. In other embodiment, the invention pertains to a full length human protein which is substantially homologous to the entire amino acid sequence of SEQ ID NO:2.

Biologically active portions of the EMI1 protein include peptides comprising amino acid sequences derived from the amino acid sequence of the EMI1 protein, e.g., the amino acid sequence shown in SEQ ID NO:2 or the amino acid sequence of a protein homologous to the EMI1 protein, which include less amino acids than the full length EMI1 protein or the full length protein which is homologous to the EMI1 protein, and exhibit at least one activity of the EMI1 protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a WW domain, with at least one activity of the EMI1 protein. Preferably, the domain is a WW domain derived from a human and is at least about 55%, preferably at least about 60–65%, even more preferably at least about 70–75%, and most preferably at least about 80–90% or more homologous to SEQ ID NO:4. If the WW domain is derived from a nonmammal, it is preferably at least about 75%, preferably at least about 80–85%, and most preferably at least about 90–95% or more homologous to SEQ ID NO:4. In a preferred embodiment, the biologically active portion of the protein which includes the WW domain can modulate the activity of a protein having a PY motif and/or modulate a TGF-$\beta$ response in a TGF-$\beta$ responsive cell, e.g., an endothelial cell, to thereby beneficially affect the TGF-$\beta$ responsive cell. In a preferred embodiment, the biologically active portion comprises the WW domain of EMI1 as represented by amino acid residues 300 to 335 of SEQ ID NO:2 and SEQ ID NO:4. Moreover, other biologically active portions, in which other regions of the protein are deleted, can be prepared by recombinant techniques and evaluated for one or more of the activities described herein. Preferably, the biologically active portions of the EMI1 protein include one or more selected domains/motifs or portions thereof having biological activity.

EMI1 proteins are preferably produced by recombinant DNA techniques. For example, a nucleic acid molecule encoding the protein is cloned into an expression vector (as described above), the expression vector is introduced into a host cell (as described above) and the EMI1 protein is expressed in the host cell. The EMI1 protein can then be isolated from the cells by an appropriate purification scheme using standard protein purification techniques. Alternative to recombinant expression, an EMI1 protein, polypeptide, or peptide can be synthesized chemically using standard peptide synthesis techniques. Moreover, native EMI1 protein can be isolated from cells (e.g., endothelial cells), for example using an anti-EMI1 antibody (described further below).

The invention also provides EMI1 chimeric or fusion proteins. As used herein, an EMI1 "chimeric protein" or "fusion protein" comprises an EMI1 polypeptide operatively linked to a non-EMI1 polypeptide. An "EMI1 polypeptide" refers to a polypeptide having an amino acid sequence corresponding to EMI1, whereas a "non-EMI1 polypeptide" refers to a polypeptide having an amino acid sequence corresponding to a protein which is not substantially homologous to the EMI1 protein, e.g., a protein which is different from the EMI1 protein and which is derived from the same or a different organism. Within the fusion protein, the term "operatively linked" is intended to indicate that the EMI1 polypeptide and the non-EMI1 polypeptide are fused in-frame to each other. The non-EMI1 polypeptide can be fused to the N-terminus or Cterminus of the EMI1 polypeptide. For example, in one embodiment the fusion protein is a GST-EMI1 fusion protein in which the EMI1 sequences are fused to the C-terminus of the GST sequences. Such fusion proteins can facilitate the purification of recombinant EMI1. In another embodiment, the fusion protein is an EMI1 protein containing a heterologous signal sequence at its N-terminus. In certain host cells (e.g., mammalian host cells), expression and/or secretion of EMI1 can be increased through use of a heterologous signal sequence.

Preferably, an EMI1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An EMI1encoding nucleic acid can be cloned into such an expression vector such that the fusion moiety is linked in-frame to the EMI1 protein.

The present invention also pertains to homologues of the EMI1 proteins which function as either an EMI1 agonist (mimetic) or an EMI1 antagonist. In a preferred embodiment, the EMI1 agonists and antagonists stimulate or inhibit, respectively, a subset of the biological activities of the naturally occurring form of the EMI1 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the EMI1 protein.

Homologues of the EMI1 protein can be generated by mutagenesis, e.g., discrete point mutation or truncation of the EMI1 protein. As used herein, the term "homologue" refers to a variant form of the EMI1 protein which acts as an agonist or antagonist of the activity of the EMI1 protein. An agonist of the EMI1 protein can retain substantially the same, or a subset, of the biological activities of the EMI1 protein. An antagonist of the EMI1 protein can inhibit one or more of the activities of the naturally occurring form of the EMI1 protein, by, for example, competitively binding to a downstream or upstream member of the EMI1 cascade which includes the EMI1 protein. Thus, the mammalian EMI1 protein and homologues thereof of the present invention can be either positive or negative regulators of TGF-$\beta$ responses in TGF-$\beta$ responsive cells.

In an alternative embodiment, homologues of the EMI1 protein can be identified by screening combinatorial libraries of mutants, e.g., truncation mutants, of the EMI1 protein for EMI1 protein agonist or antagonist activity. In one embodiment, a variegated library of EMI1 variants is generated by combinatorial mutagenesis at the nucleic acid level and is encoded by a variegated gene library. A variegated library of EMI1 variants can be produced by, for example, enzymatically ligating a mixture of synthetic oligonucleotides into gene sequences such that a degenerate set of potential EMI1 sequences is expressible as individual polypeptides, or alternatively, as a set of larger fusion proteins (e.g., for phage display) containing the set of EMI1 sequences therein. There are a variety of methods which can be used to produce libraries of potential EMI1 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential EMI1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the EMI1 protein coding can be used to generate a variegated population of EMI1 fragments for screening and subsequent selection of homologues of an EMI1 protein. In one embodiment, a library of coding sequence fragments can be generated by treating a double stranded PCR fragment of an EMI1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the EMI1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of EMI1 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify EMI1 homologues (Arkin and Yourvan (1992) *PNAS* 89:7811–7815; Delgrave et al. (1993) *Protein Engineering* 6(3):327–331).

In one embodiment, cell based assays can be exploited to analyze a variegated EMI1 library. For example, a library of expression vectors can be transfected into a cell line ordinarily responsive to a particular TGF-β. The transfected cells are then contacted with the TGF-β and the effect of the EMI1 mutant on signaling by TGF-β can be detected, e.g., by measuring $^3$[H]thymidine incorporation. Plasmid DNA can then be recovered from the cells which score for inhibition, or alternatively, potentiation of TGF-β induction, and the individual clones further characterized.

An isolated EMI1 protein, or a portion or fragment thereof, can be used as an immunogen to generate antibodies that bind EMI1 using standard techniques for polyclonal and monoclonal antibody preparation. The full-length EMI1 protein can be used or, alternatively, the invention provides antigenic peptide fragments of EMI1 for use as immunogens. The antigenic peptide of EMI1 comprises at least 8 amino acid residues of the amino acid sequence shown in SEQ ID NO:2 and encompasses an epitope of EMI1 such that an antibody raised against the peptide forms a specific immune complex with EMI1. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of EMI1 that are located on the surface of the protein, e.g., hydrophilic regions.

An EMI1 immunogen typically is used to prepare antibodies by immunizing a suitable subject, (e.g., rabbit, goat, mouse or other mammal) with the immunogen. An appropriate immunogenic preparation can contain, for example, recombinantly expressed EMI1 protein or a chemically synthesized EMI1 peptide. The preparation can further include an adjuvant, such as Freund's complete or incomplete adjuvant, or similar immunostimulatory agent. Immunization of a suitable subject with an immunogenic EMI 1 preparation induces a polyclonal anti-EMI1 antibody response.

Accordingly, another aspect of the invention pertains to anti-EMI1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as EMI1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind EMI1. The term "monoclonal antibody" or "monoclonal antibody composition", as used herein, refers to a population of antibody molecules that contain only one species of an antigen binding site capable of immunoreacting with a particular epitope of EMI1. A monoclonal antibody composition thus typically displays a single binding affinity for a particular EMI1 protein with which it immunoreacts.

Polyclonal anti-EMI1 antibodies can be prepared as described above by immunizing a suitable subject with an EMI1 immunogen. The anti-EMI1 antibody titer in the immunized subject can be monitored over time by standard techniques, such as with an enzyme linked immunosorbent assay (ELISA) using immobilized EMI1. If desired, the antibody molecules directed against EMI1 can be isolated from the mammal (e.g., from the blood) and further purified by well known techniques, such as protein A chromatography to obtain the IgG fraction. At an appropriate time after immunization, e.g., when the anti-EMI1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* .255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al.

(1977) *Somatic Cell Genet.* 3:231–36). Briefly, an immortal cell line (typically a myeloma) is fused to lymphocytes (typically splenocytes) from a mammal immunized with an EMI1 immunogen as described above, and the culture supernatants of the resulting hybridoma cells are screened to identify a hybridoma producing a monoclonal antibody that binds EMI1.

Any of the many well known protocols used for fusing lymphocytes and immortalized cell lines can be applied for the purpose of generating an anti-EMI1 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind EMI1, e.g., using a standard ELISA assay.

Alternative to preparing monoclonal antibody-secreting hybridomas, a monoclonal anti-EMI1 antibody can be identified and isolated by screening a recombinant combinatorial immunoglobulin library (e.g., an antibody phage display library) with EMI1 to thereby isolate immunoglobulin library members that bind EMI1. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram ct al. (1992) *PNAS* 89:3576–3580; Garrad et al. (1991) *Bio/Technology* 9:1373–1377; Hoogenboom et al. (1 991) *Nuc. Acid Res.* 19:4133–4137; Barbas et al. (1991) *PNAS* 88:7978–7982; and McCafferty et al. *Nature* (1990) 348:552–554.

Additionally, recombinant anti-EMI1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1 043; Liu et al. (1987) *PNAS* 84:3439–3443; Liu et al. (1987) *J. Immunol.* 139:3521–3526; Sun et al. (1987) *PNAS* 84:214–218; Nishimura et al. (1987)i Canc. Res. 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *Bio Techniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-EMI1 antibody (e.g., monoclonal antibody) can be used to isolate EMI 1 by standard techniques, such as affinity chromatography or immunoprecipitation. An anti-EMI1 antibody can facilitate the purification of natural EMI1 from cells and of recombinantly produced EMI1 expressed in host cells. Moreover, an anti-EMI1 antibody can be used to detect EMI1 protein (e.g., in a cellular lysate or cell supernatant) in order to evaluate the abundance and pattern of expression of the EMI1 protein. Anti-EMI1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

IV. Pharmaceutical Compositions

The EMI1 nucleic acid molecules, EMI1 proteins, EMI1 modulators, and anti-EMI1 antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an EMI1 protein or anti-EMI1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, modulators, and antibodies described herein can be used in one or more of the following methods: 1) drug screening assays; 2) diagnostic assays; and 3) methods of treatment. An EMI1 protein of the invention has one or more of the activities described herein and can thus be used to, for example, modulate a TGF-β response in a TGF-β responsive cell. The isolated nucleic acid molecules of the invention can be used to express EMI1 protein (e.g., via a recombinant expression vector in a host cell in gene therapy applications), to detect EMI1 mRNA (e.g., in a biological sample) or a genetic lesion in an EMI 1 gene, and to modulate EMI1 activity, as described further below. In addition, the EMI1 proteins can be used to screen drugs or compounds which modulate EMI1 protein activity as well as to treat disorders characterized by insufficient production of EMI1 protein or production of EMI1 protein forms which have decreased activity compared to wild type EMI1. Moreover, the anti-EMI1 antibodies of the invention can be used to detect and isolate EMI1 protein and modulate EMI1 protein activity.

a. Drug Screening Assays:

The invention provides methods for identifying compounds or agents which can be used to treat disorders characterized by (or associated with) aberrant or abnormal EMI nucleic acid expression and/or EMI1 protein activity. These methods are also referred to herein as drug screening assays and typically include the step of screening a candidate/test compound or agent for the ability to interact with (e.g., bind to) an EMI1 protein, to modulate the interaction of an EMI1 protein and a target molecule, and/or to modulate EMI1 nucleic acid expression and/or EMI1 protein activity. Candidate/test compounds or agents which have one or more of these abilities can be used as drugs to treat disorders characterized by aberrant or abnormal EMI nucleic acid expression and/or EMI1 protein activity. Candidate/test compounds such as small molecules, e.g., small organic molecules, and other drug candidates can be obtained, for example, from combinatorial and natural product libraries.

In one embodiment, the invention provides assays for screening candidate/test compounds which interact with (e.g., bind to) EMI1 protein. Typically, the assays are cell-free assays which include the steps of combining an EMI1 protein or a biologically active portion thereof, and a candidate/test compound, e.g., under conditions which allow for interaction of (e.g., binding of) the candidate/test compound to the EMI1 protein or portion thereof to form a complex, and detecting the formation of a complex, in which the ability of the candidate compound to interact with (e.g., bind to) the EMI1 protein or portion thereof is indicated by the presence of the candidate compound in the complex. Formation of complexes between the EMI1 protein and the candidate compound can be quantitated, for example, using standard immunoassays.

In another embodiment, the invention provides screening assays to identify candidate/test compounds which modulate (e.g., stimulate or inhibit) the interaction (and most likely EMI1 activity as well) between an EMI1 protein and a molecule (target molecule) with which the EMI1 protein normally interacts. Examples of such target molecules includes proteins in the same signaling path as the EMI1 protein, e.g., proteins which may function upstream (including both stimulators and inhibitors of activity) or downstream of the EMI1 protein in the TGF-β signaling pathway, e.g., an MADR protein. Typically, the assays are cell-free assays which include the steps of combining an EMI1 protein or a biologically active portion thereof, an EMI1 target molecule (e.g., an EMI1 ligand) and a candidate/test compound, e.g., under conditions wherein but for the presence of the candidate compound, the EMI1 protein or biologically active portion thereof interacts with (e.g., binds to) the target molecule, and detecting the formation of a complex which includes the EMI1 protein and the target molecule or detecting the interaction/reaction of the EMI1 protein and the target molecule. Detection of complex formation can include direct quantitation of the complex by, for example, measuring inductive effects of the EMI1 protein. A statistically significant change, such as a decrease, in the interaction of the EMI1 and target molecule (e.g., in the formation of a complex between the EMI1 and the target molecule) in the presence of a candidate compound (relative to what is detected in the absence of the candidate compound) is indicative of a modulation (e.g., stimulation or inhibition) of the interaction between the EMI1 protein and the target molecule. Modulation of the formation of complexes between the EMI1 protein and the target molecule can be quantitated using, for example, an immunoassay.

To perform the above drug screening assays, it is desirable to immobilize either EMI1 or its target molecule to facilitate separation of complexes from uncomplexed forms of one or both of the proteins, as well as to accommodate automation of the assay. Interaction (e.g., binding of) of EMI1 to a target molecule, in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the protein to be bound to a matrix. For example, glutathione-S-transferase/EMI1 fusion proteins can be adsorbed onto glutathione sepharose beads (Sigma Chemical, St. Louis, Mo.) or glutathione derivatized microtitre plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of EMI1 -binding protein found in the bead fraction quantitated from the gel using standard electrophoretic techniques.

Other techniques for immobilizing proteins on matrices can also be used in the drug screening assays of the invention. For example, either EMI1 or its target molecule can be immobilized utilizing conjugation of biotin and streptavidin. Biotinylated EMI1 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with EMI1 but which do not interfere with binding of the protein to its target molecule can be derivatized to the wells of the plate, and EMI1 trapped in the wells by antibody conjugation. As described above, preparations of a EMI1 -binding protein and a candidate compound are incubated in the EMI1 -presenting wells of the plate, and the amount of complex trapped in the well can be quantitated. Methods for detecting such complexes, in addition to those described above for the GST-immobilized complexes, include immunodetection of complexes using antibodies reactive with the EMI1 target molecule, or which are reactive with EMI1 protein and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal EMI1 nucleic acid expression or EMI1 protein activity. This method typically includes the step of assaying the ability of the compound or agent to modulate the expression of the EMI1 nucleic acid or the activity of the EMI1 protein thereby identifying a compound for treating a disorder characterized by aberrant or abnormal EMI1 nucleic acid expression or EMI1 protein activity. Disorders characterized by aberrant or abnormal EMI1 nucleic acid expression or EMI1 protein activity are described herein. Methods for assaying the ability of the compound or agent to modulate the expression of the EMI1 nucleic acid or activity of the EMI1 protein are typically cell-based assays. For example, cells which are sensitive to ligands, e.g., TGF-β, which transduce signals via a pathway involving EMI1 can be induced to overexpress an EMI1 protein in the presence and absence of a candidate compound. Candidate compounds which produce a statistically significant change in EMI1 -dependent responses (either stimulation or inhibition) can be identified. In one embodiment, expression of the EMI1 nucleic acid or activity of an EMI1 protein is modulated in cells and the effects of candidate compounds on the readout of interest (such as rate of cell proliferation or differentiation) are measured. For example, the expression of genes which are up- or down-regulated in response to an EMI1 -dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of EMI1 or EMI1 target molecules can also be measured, for example, by immunoblotting.

Alternatively, modulators of EMI1 expression (e.g., compounds which can be used to treat a disorder characterized by aberrant or abnormal EMI1 nucleic acid expression or EMI1 protein activity) can be identified in a method wherein a cell is contacted with a candidate compound and the expression of EMI1 mRNA or protein in the cell is determined. The level of expression of EMI1 mRNA or protein in the presence of the candidate compound is compared to the level of expression of EMI1 mRNA or protein in the absence of the candidate compound. The candidate compound can then be identified as a modulator of EMI1 nucleic acid expression based on this comparison and be used to treat a disorder characterized by aberrant EMI1 nucleic acid expression. For example, when expression of EMI1 mRNA or protein is greater (statistically significantly greater) in the presence of the candidate compound than in its absence, the candidate compound is identified as a stimulator of EMI1 mRNA or protein expression. Alternatively, when expression of EMI1 mRNA or protein is less (statistically significantly less) in the presence of the candidate compound than in its absence, the candidate compound is identified as an inhibitor of EMI1 mRNA or protein expression. The level of EMI1 mRNA or protein expression in the cells can be determined by methods described herein for detecting EMI1 mRNA or protein.

In yet another aspect of the invention, the EMI1 proteins can be used as "bait proteins" in a two-hybrid assay (see, e.g., U.S. Pat. No. 5,283,317; Zervos et al. (1993) *Cell* 72:223–232; Maduraet al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with EMI1 ("EMI1-binding proteins" or "EMI1-bp") and modulate EMI1 protein activity. Such EMI1 -binding proteins are also likely to be involved in the propagation of signals by the EMI1 proteins as, for example, upstream or downstream elements of the EMI1 pathway.

The two-hybrid system is based on the modular nature of most transcription factors, which consist of separable DNA-binding and activation domains. Briefly, the assay utilizes two different DNA constructs. In one construct, the gene that codes for EMI1 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an EMI1 -dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with EMI1.

Modulators of EMI1 protein activity and/or EMI1 nucleic acid expression identified according to these drug screening assays can be to treat, for example, cardiovascular diseases or disorders such as atherosclerosis, ischemia/reperfusion, hypertension, and restenosis. Examples of other cardiovascular diseases or disorders which can be treated using modulators of EMI1 protein activity and/or nucleic acid expression are described in Robbins, S. L. et al. eds. Pathologic Basis of Disease (W. B. Saunders Company, Philadelphia, Pa. 1984) 502–547. These methods of treatment include the steps of administering the modulators of EMI1 protein activity and/or nucleic acid expression, e.g., in a pharmaceutical composition as described in subsection IV above, to a subject in need of such treatment, e.g., a subject with cardiovascular disease.

b. Diagnostic Assays:

The invention further provides a method for detecting the presence of EMI1 in a biological sample. The method involves contacting the biological sample with a compound or an agent capable of detecting EMI1 protein or mRNA such that the presence of EMI1 is detected in the biological sample. A preferred agent for detecting EMI1 mRNA is a labeled or labelable nucleic acid probe capable of hybridizing to EMI 1 mRNA. The nucleic acid probe can be, for example, the full-length EMI1 cDNA of SEQ ID NO:1, or a portion thereof, such as an oligonucleotide of at least 15, 30, 50, 100, 250 or 500 nucleotides in length and sufficient to specifically hybridize under stringent conditions to EMI1 mRNA. A preferred agent for detecting EMI1 protein is a labeled or labelable antibody capable of binding to EMI1 protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect EMI1 mRNA or protein in a biological sample in vitro as well as in vivo. For example, in vitro techniques for detection of EMI1 mRNA include Northern hybridizations and in situ hybridizations. In vitro techniques for detection of EMI1 protein include enzyme linked immunosorbent assays (ELISAs), Western blots, immunoprecipitations and immunofluorescence. Alternatively, EMI1 protein can be detected in vivo in a subject by introducing into the subject a labeled anti-EMI1 antibody. For example, the antibody can be labeled with a radioactive marker whose presence and location in a subject can be detected by standard imaging techniques.

In one preferred embodiment of the detection method, the biological sample is a endothelial cell sample. The endothelial cell sample can comprise vascular tissue or a suspension of endothelial cells. A tissue section, for example, a freeze-dried or fresh frozen section of vascular tissue removed from a patient, can be used as the endothelial cell sample. Alternatively, the biological sample can comprise a biological fluid obtained from a subject having a cardiovascular disorder. In another preferred embodiment of the detection method, the biological sample is an epithelial cell sample (e.g., a sample which includes gut-derived epithelial cells). A tissue section, for example, a freeze-dried or fresh frozen section of epithelial cell-based tumor tissue (e.g., carcinoma tissue) removed from a patient, can be used as the epithelial cell sample.

The invention also encompasses kits for detecting the presence of EMI1 in a biological sample. For example, the kit can comprise a labeled or labelable compound or agent capable of detecting EMI1 protein or mRNA in a biological sample; means for determining the amount of EMI1 in the sample; and means for comparing the amount of EMI1 in the sample with a standard. The compound or agent can be packaged in a suitable container. The kit can further comprise instructions for using the kit to detect EMI1 mRNA or protein.

The methods of the invention can also be used to detect genetic lesions in a EMI1 gene, thereby determining if a subject with the lesioned gene is at risk for a disorder characterized by aberrant or abnormal EMI1 nucleic acid expression or EMI1 protein activity as defined herein. In preferred embodiments, the methods include detecting, in a sample of cells from the subject, the presence or absence of a genetic lesion characterized by at least one of an alteration affecting the integrity of a gene encoding an EMI1 protein, or the misexpression of the EMI1 gene. For example, such genetic lesions can be detected by ascertaining the existence of at least one of 1) a deletion of one or more nucleotides from an EMI1 gene; 2) an addition of one or more nucleotides to an EMI1 gene; 3) a substitution of one or more nucleotides of an EMI1 gene, 4) a chromosomal rearrangement of an EMI1 gene; 5) an alteration in the level of a messenger RNA transcript of an EMI1 gene, 6) aberrant modification of an EMI1 gene, such as of the methylation pattern of the genomic DNA, 7) the presence of a non-wild type splicing pattern of a messenger RNA transcript of an EMI1 gene, 8) a non-wild type level of an EMI1 -protein, 9) allelic loss of an EMI1 gene, and 10) inappropriate post-translational modification of an EMI1 -protein. As described herein, there are a large number of assay techniques known in the art which can be used for detecting lesions in an EMI1 gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1 994) *PNAS* 91:360–364), the latter of which can be particularly useful for detecting point mutations in the EMI1-gene (see Abravaya et al. (1995) *Nucleic Acids Res*.23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an EMI1 gene under conditions such that hybridization and amplification of the EMI1 -gene (if present) occurs, and detecting the presence or absence of an amplification product, or detecting the size of the amplification product and comparing the length to a control sample.

In an alternative embodiment, mutations in an EMI1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the EMI1 gene and detect mutations by comparing the sequence of the sample EMI1 with the corresponding wild-type (control) sequence. Examples of sequencing reactions include those based on techniques developed by Maxim and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1 996) *Adv. Chromalogr.* 36:127–162; and Griffin et al. (1 993) *Appl. Biochem. Biotechnol.* 38:147–159).

Other methods for detecting mutations in the EMI1 gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton (1993) *Mutat Res* 285:125–144; and Hayashi (1992) *Genet Anal Tech Appl* 9:73–79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) aberrant or abnormal EMI1 nucleic acid expression and/or EMI1 protein activity. These methods include the step of administering an EMI1 modulator to the subject such that treatment occurs. The language "aberrant or abnormal EMI1 expression" refers to expression of a non-wild-type EMI1 protein or a non-wild-type level of expression of an EMI1 protein. Aberrant or abnormal EMI1 activity refers to a non-wild-type EMI1 activity or a nonwild-type level of EMI1 activity. As the EMI1 protein is involved in the TGF-β signaling pathway, aberrant or abnormal EMI1 activity or expression interferes with the normal TGF-β effects on TGF-β responsive cells. Non-limiting examples of disorders or diseases characterized by or associated with abnormal or aberrant EMI1 activity or expression include cardiovascular disorders and proliferative disorders (e.g., cancers). Cardiovascular disorders are disorders which detrimentally affect normal cardiovascular function. Examples of cardiovascular disorders include atherosclerosis, ischemia/reperfusion, hypertension, restenosis, and arterial inflammation. Proliferative disorders are disorders which are associated with uncontrolled or undesirable cell proliferation. Examples of proliferative disorders include proliferative disorders of epithelial cells, e.g., proliferative disorders of gut derived cells, e.g., pancreatic cancer and colorectal cancer. Additional methods of the invention include methods for treating a subject having a disorder characterized by aberrant EMI1 activity or expression. These methods include administering to the subject an EMI1 modulator such that treatment of the subject occurs. The terms "treating" or "treatment", as used herein, refer to reduction or alleviation of at least one adverse effect or symptom of a disease or disorder, e.g., a disease or disorder characterized by or associated with abnormal or aberrant EMI1 protein activity or EMI1 nucleic acid expression.

As used herein, an EMI1 modulator is a molecule which can modulate EMI1 nucleic acid expression and/or EMI1 protein activity. For example, an EMI1 modulator can modulate, e.g., upregulate (activate) or downregulate (suppress), EMI1 nucleic acid expression. In another example, an EMI1 modulator can modulate (e.g., stimulate or inhibit) EMI1 protein activity. If it is desirable to treat a disease or disorder characterized by (or associated with) aberrant or abnormal (non-wild-type) EMI1 nucleic acid expression and/or EMI1 protein activity by inhibiting EMI1 nucleic acid expression, an EMI1 modulator can be an antisense molecule, e.g., a ribozyme, as described herein. Examples of antisense molecules which can be used to inhibit EMI1 nucleic acid expression include antisense molecules which are complementary to a portion of the 5' untranslated region of SEQ ID NO:1 which also includes the start codon and antisense molecules which are complementary to a portion of the 3' untranslated region of SEQ ID NO:1. An example of an antisense molecule which is complementary to a portion of the 5' untranslated region of SEQ ID NO:1 and which also includes the start codon is a nucleic acid molecule which includes nucleotides which are complementary to nucleotides 58 to 79 of SEQ ID NO:1. This antisense molecule has the following nucleotide sequence: 5'CGTCGAAGTGCCACTACTATAC3' (SEQ ID NO:5). An example of an antisense molecule which is complementary to a portion of the 3' untranslated region of SEQ ID NO:1 is a nucleic acid molecule which includes nucleotides which are complementary to nucleotides 1102 to 1118 of SEQ ID NO:1. This antisense molecule has the following sequence: 5'AGTTCCAGAGTCTCAGG 3' (SEQ ID NO:6). An additional example of an antisense molecule which is complementary to a portion of the 3' untranslated region of SEQ ID NO:1 is a nucleic acid molecule which includes nucleotides which are complementary to nucleotides 1169 to 1188 of SEQ ID NO:1. This antisense molecule has the following sequence: 5' ACGTCACTGTGCTATGCTAC 3'(SEQ ID NO:7). An EMI1 modulator which inhibits EMI1 nucleic acid expression can also be a small molecule or other drug, e.g., a small molecule or drug identified using the screening assays described herein, which inhibits EMI1 nucleic acid expression. If it is desirable to treat a disease or disorder characterized by (or associated with) aberrant or abnormal (non-wild-type) EMI1 nucleic acid expression and/or EMI1 protein activity by stimulating EMI1 nucleic acid expression, an EMI1 modulator can be, for example, a nucleic acid molecule encoding EMI1 (e.g., a nucleic acid molecule comprising a nucleotide sequence homologous to the nucleotide sequence of SEQ ID NO:1) or a small molecule or other drug, e.g., a small molecule (peptide) or drug identified using the screening assays described herein, which stimulates EMI1 nucleic acid expression.

Alternatively, if it is desirable to treat a disease or disorder characterized by (or associated with) aberrant or abnormal (non-wild-type) EMI1 nucleic acid expression and/or EMI1 protein activity by inhibiting EMI1 protein activity, an EMI1 modulator can be an anti-EMI1 antibody or a small molecule or other drug, e.g., a small molecule or drug identified using the screening assays described herein, which inhibits EMI1 protein activity. If it is desirable to treat a disease or disorder characterized by (or associated with) aberrant or abnormal (non-wild-type) EMI1 nucleic acid expression and/or EMI1 protein activity by stimulating EMI1 protein activity, an EMI1 modulator can be an active EMI1 protein or portion thereof (e.g., an EMI1 protein or portion thereof having an amino acid sequence which is homologous to the amino acid sequence of SEQ ID NO:2 or a portion thereof) or a small molecule or other drug, e.g., a small molecule or drug identified using the screening assays described herein, which stimulates EMI1 protein activity.

In addition, a subject having a cardiovascular disorder can be treated according to the present invention by administering to the subject an EMI1 protein or portion or a nucleic acid encoding an EMI1 protein or portion thereof such that treatment occurs. Similarly, a subject having a proliferative disorder can be treated according to the present invention by administering to the subject an EMI1 protein or portion thereof or a nucleic acid encoding an EMI1 protein or portion thereof such that treatment occurs.

Other aspects of the invention pertain to methods for modulating a cell associated activity. These methods include contacting the cell with an agent (or a composition which includes an effective amount of an agent) which modulates EMI1 activity or EMI1 expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, and cell survival. In a preferred embodiment, the cell is a TGF-β responsive cell, e.g., a cell which responds to TGF-β signaling through a pathway which involves EMI1. Examples of cells which respond to TGF-β signaling through a pathway which involves EMI1 are endothelial cells and epithelial cells. The term "altered" as used herein refers to a change, e.g., an increase or decrease, of a cell associated activity. In one embodiment, the agent stimulates EMI1 protein activity or EMI1 nucleic acid expression. Examples of such stimulatory agents include an active EMI1 protein, a nucleic acid molecule encoding EMI1 that has been introduced into the cell, and a modulatory agent which stimulates EMI1 protein activity or EMI nucleic acid expression and which is identified using the drug screening assays described herein. In another embodiment, the agent inhibits EMI1 protein activity or EMI1 nucleic acid expression. Examples of such inhibitory agents include an antisense EMI1 nucleic acid molecule, an anti-EMI1 antibody, and a modulatory agent which inhibits EMI1 protein activity or EMI1 nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant EMI1 activity or expression.

A nucleic acid molecule, a protein, an EMI1 modulator etc. used in the methods of treatment can be incorporated into an appropriate pharmaceutical composition described herein and administered to the subject through a route which allows the molecule, protein, modulator etc. to perform its intended function. Examples of routes of administration are also described herein under subsection IV.

This invention is further illustrated by the following examples which should not be construed as limiting. The contents of all references, patent applications, patents, and published patent applications cited throughout this application are hereby incorporated by reference.

EXAMPLES

The following materials and methods were used in the Examples:

Yeast Strains, Media, and Microbiological Techniques

Yeast strains, *E. coli* strains, and plasmids used in this work are listed in Tables 1–3 below. Standard yeast media including synthetic complete medium lacking L-leucine, L-tryptophan, and L-histidine were prepared and yeast genetic manipulations were performed as described (Sherman (1991) *Meth. Enzymol.* 194:3–21). Yeast transformations were performed using standard protocols (Gietz et al. (1992) *Nucleic Acids Res.* 20:1425; Ito et al (1983) *J. Bacteriol.* 153:163–168). Plasmid DNAs were isolated from yeast strains by a standard method (Hoffman and Winston (1987) *Gene* 57:267–272).

TABLE 1

*E. Coli* Strains

| *E. coli* Strain | Genotype | Source or Derivation |
|---|---|---|
| PEB199 | F- ompT hsdS$_B$ (r$_B$- m$_B$-) gal dcmlon | BL21 lon (Studier (1991) J. Mol. Biol. 219:37–44) derivative. |

TABLE 2

Yeast Strains

| Yeast Strain | Genotype | Source or Derivation |
|---|---|---|
| HF7c | MATa ura3-52 his3-200 lys2-801 ade2-101 trpl-901 leu2-3, 112 gal4-542 gal80-538 LYS2: :GAL1$_{UAS}$-GAL1$_{TATA}$-HIS3 URA3: :GAL4$_{17mers(x3)}$-CyC1$_{TATA}$-lacz | Feilotter et al. (1994) Nucleic Acids Res. 22:1502–1503 |
| Y187 | MATα gal4 gal80 his3 trp1-901 ade2-101 ura3-52 leu2-3,112 met-URA3: :GAL→lacZ | Bai, C. and Elledge, S. J. (1995) Methods Enzymol. 273:331–347. |
| TB35 | HF7c + pMB155 | Prepared for experiments described herein. |
| TB30 | HF7c + pYCHD534b | Applicants' collection. |
| TB32 | HF7c + PYCFXO11 | Applicants' collection. |
| TB29 | HF7c + pYCHXO1 | Applicants' collection. |
| TB19 | HF7c + p53 | Applicants' collection. |
| TB17 | HF7c + pGBT9 | Applicants' collection. |
| TB39 | HF7c + pMB146 | Prepared for experiments described herein. |
| TF4 | Y187 + pSV40 | Prepared for experiments described herein. |
| TB40 | HF7c + pMB147 | Prepared for experiments described herein |
| TB41 | HF7c + pMB148 | Prepared for experiments described herein |

TABLE 3

Plasmids

| Plasmid Name | Description | Source or Derivation |
|---|---|---|
| pACTII | GAL4(768-881) fusion vector | Bai, C. and Elledge, S. J. (1995) Methods Enzymol. 273:331–347. |
| PGBT9 | GAL4(1-147) fusion vector marked with TRP1 and amp$^r$ | Bartel et al. (1993) Cellular Interactions in Development 153–159 |
| pMB155 | coding sequence of the fchd540 gene product (MADR7) cloned in-frame into pGBT9 | Prepared for experiments described herein. |
| pYCHD534b | coding sequence of the fchd534 gene product (MADR6) cloned in-frame into pGBT9 | Applicants' collection. |
| pYCFZO11 | Drosophila MAD coding sequence cloned in-frame into pGBT9 | Applicants' collection |
| PYCHZO1 | DPC4 coding sequence cloned in-frame into pGBT9 | Applicants' collection. |
| p53 | p53 control plasmid | HybriZAP Two-Hybrid Vector Kit (Stratagene, LaJolla, CA) |
| pSV40 | SV40 control plasmid | HybriZAP Two-Hybrid Vector Kit (Stratagene, LaJolla, CA) |
| PGEX-5X-2 | GST gene fusion vector | Pharmacia Biotech, Inc. (Piscataway, NJ) |
| pMB140B | EMI1$_{138-335}$ cloned in pGEX-5x-2 | Prepared for experiments described herein. |
| pMB146 | PY motif of the fchd540 gene product (MADR7) cloned in pGBT9 | Prepared for experiments described herein. |
| pN8epsilon-534 (MADR6)-myc | coding sequence of the fchd534 gene product (MADR6) in pN8epsilon-myc | Prepared for experiments described herein. |
| pN8epsilon-540 (MADR7)-myc | coding sequence of the fchd540 gene product (MADR7) in pN8epsilon-myc | Prepared for experiments described herein. |
| pN8epsilon-EMI1-HA | EMI1 coding sequence in pN8epsilon-myc | Prepared for experiments described herein. |
| pN8epsilon myc | CMV promoter-driven mammalian expression vector that fuses three copies of the myc epitope tag to test proteins | Applicants' collection |
| pN8epsilon-HA | CMV promoter-driven mammalian expression vector that fuses three copies of the HA epitope tag to test proteins | Applicants' collection |
| pMB147 | P→A mutant of the PY domain of the fchd540 gene product (MADR7) | Prepared for experiments described herein. |
| pMB148 | Y→A mutant of the PY domain of the fchd540 gene product (MADR7) | Prepared for experiments described herein. |

Plasmid and Yeast Strain Construction

The coding region of the human fchd540 gene product (also known as MADR7) was amplified by PCR and cloned in-frame into pGBT9 resulting in plasmid pMB155. pMBI55 was transformed into two-hybrid screening strain HF7c, and one resulting transformant was designated TB35.

The coding region of the human fchd534 gene product (also known as MADR6) was amplified by PCR and cloned in-frame into pGBT9 resulting in plasmid pYCHD534b. pYCHD534b was transformed into two-hybrid screening strain HF7c, and one resulting transformant was designated TB30.

The coding region of the Drosophila MAD gene (Sekelsky et al. (1995) Genetics 139:1347–1358.) was amplified by PCR and cloned in-frame into pGBT9 resulting in plasmid pYCFX011. pYCFX011 was transformed into two-hybrid screening strain HF7c, and one resulting transformant was designated TB32.

The coding region of the DPC4 gene (Hahn et al. (1996) Science 271:350–353.) was amplified by PCR and cloned in-frame into pGBT9 resulting in plasmid pYCHX01. pYCHX01 was transformed into two-hybrid screening strain HF7c, and one resulting transformant was designated TB29.

DNA encoding amino acids 138–335 of EMI1 was amplified by PCR and cloned in-frame into pGEX-5X-2 resulting in plasmid pMB140B.

Complementary oligonucleotides encoding the 16 amino acid PY motif of the fchd540 gene product (MADR7) (RLCELESPPPPYSRYP (SEQ ID NO:8)) were synthesized, annealed, and cloned into pGBT9 resulting in plasmid pMB146.

The coding region of the human fchd534 gene (MADR6) was amplified by PCR and cloned in-frame into pN8cpsilon-myc resulting in plasmid pN8epsilon-fchd534 gene-myc.

The coding region of the human fchd540 gene (MADR7) was amplified by PCR and cloned in-frame into pN8epsilon-myc resulting in plasmid pN8epsilon-fchd540 gene-myc.

The coding region of human EMI1 was amplified by PCR and cloned in-frame into pN8epsilon-HA resulting in plasmid pN8epsilon-EMI1-HA.

Complementary oligonucleotides encoding the 16 amino acid PY motif of the fchd540 gene product (MADR7) with the proline at position 10 mutated to alanine (RLCELESPPAPYSRYP (SEQ ID NO:9)) were synthesized, annealed, and cloned into pGBT9 resulting in plasmid pMB 147.

Complementary oligonucleotides encoding the 16 amino acid PY motif of the fchd540 gene product (MADR7) with the tyrosine at position 12 mutated to alanine (RLCELESPPPPASRYP (SEQ ID NO:10)) were synthesized, annealed, and cloned into pGBT9 resulting in plasmid pMB148.

Two-Hybrid Screening

Two-hybrid screening was carried out essentially as described (Bartel et al. (1993) Cellular Interactions in Development 153–159) using MY114 as the recipient strain and a human breast two-hybrid library constructed in the lambda ACT II vector.

Beta Galactosidase Assays

The filter disk beta-galactosidase (beta-gal) assay was performed essentially as previously described (Brill et al. (1994) *Mol. Biol. Cell.* 5:297–312). Briefly, strains to be tested were grown as patches of cells on appropriate medium dictated by the experiment at 30° C. overnight. The patches or colonies of cells were replica plated to Whatman #50 paper disks (#576 from Schleicher & Schuell, Keene, N.H.) that had been placed on the test medium in petri dishes. After growth overnight at 30° C., the paper disks were removed from the plates and the cells on them were permeabilized by immediate immersion in liquid nitrogen for 30 seconds. After this treatment, the paper disks were thawed at room temperature for 20 seconds and then placed in petri dishes that contained a disk of Whatman #3 paper (#593 from Schleicher & Schuell, Keene, N.H.) saturated with 2.5 ml of Z buffer containing 37 $\mu$l of 2% weight per volume of the chromogenic beta-gal substrate X-gal. The permeabilized strains on the paper disks were incubated at 30° C. and inspected at timed intervals for the blue color diagnostic of beta-gal activity in this assay. The assay was stopped by removing the paper disk containing the patches of cells and air drying it.

Expression and Purification of Recombinant EMI1 Protein

An overnight culture of *E. Coli* strain PEB199 carrying the pMB140B EMI1 GST-fusion plasmid was grown overnight in TB 100 $\mu$g/ml ampicillin medium. The following day the culture was diluted 1:10 in fresh TB 100 $\mu$g/ml ampicillin medium and grown to an $OD_{600}$ of 0.6–0.8. IPTG was added to the culture to a final concentration of 0.5–1.0 mM and the culture was then incubated for 3–4 hours at 37° C. The culture was pelleted and stored frozen (–80° C.) for 1 day. The culture was thawed and resuspended in 20–50 ml of PBS and passed through a French press 2–3 times at 20,000 psi. Disruption was monitored by taking $OD_{600}$ readings of the lysate. The lysate was centrifuged for 30 minutes at 15,000×g and the supernatant was decanted to a fresh tube. Glutathione Sepharose 4B resin (Pharmacia Biotech, Inc., Piscataway, NJ) was washed with 5–10 column volumes of PBS to remove resin storage buffer. The supernatant was added to the washed resin. The resulting slurry was added to a 50 ml conical tube and batch binding was allowed to proceed for one hour. The slurry was washed twice with 10 column volumes of PBS and then the recombinant protein was eluted with a 50 mM tris-HCl pH 8.0 buffer containing 50 mM reduced glutathione. Eluted proteins were analyzed by electrophoresis on a 14% tris glycine SDS polyacrylamide gel (Novex, San Diego, Calif.) and subsequent Coomassie staining.

Coimmunoprecipitation Analysis

Primary bovine aortic endothelial cells (BAECs) were transfected with 2 $\mu$g of pN8epsilon-fchd534 gene (MADR6)-myc or pN8epsilon-fchd540 gene (MADR7)-myc and 10 $\mu$gs of pN8epsilon-EMI1-HA using the calcium phosphate method. pN8epsilon-myc is a plasmid derived from pCI (Promega, Madison, Wis.) with the CMV promoter and three myc peptide encoding sequences such that when a cDNA is inserted, three inframe mycs are added to the amino terminus of the expressed protein. pN8epsilon-HA is identical to pN8epsilon-myc except that it contains three copies of the HA epitope tag instead of the myc epitope tag.

Forty-eight hours after transfection, cells were removed from the plates by scraping, washed with PBS, and pelleted. This pellet was resuspended in 100 $\mu$l of lysis buffer (20 mM HEPES, pH 7.5, 0.3M NaCl, 1.5mM $MgCl_2$, 0.2mM EDTA, 0.1% Triton×100) and allowed to incubate on ice for 20 minutes. Lysed cells were then spun for 15 minutes in an Eppendorf centrifuge and the resulting supernatant was added to 300 $\mu$l of equilibration buffer (20 mM HEPES, 2.5mM $MgCl_2$, 1 mM EDTA). 1 $\mu$g of mouse monoclonal antibody against HA (Boehringer Mannheim, Indianapolis Ind.) was added with 20 $\mu$l of protein G agarose and incubated overnight with shaking at 4° C. The tube was then spun and the supernatant was removed leaving the agarose beads. Beads were washed twice with wash buffer (20 mM HEPES, 0.05 M NaCl, 2.5 mM MgCl, 1 mM EDTA, 0.05% Triton×100) twice with Tris/LiCl buffer (100 mM Tris, 500 mM LiCl) and then twice again with wash buffer. Wash buffer was removed and 20 $\mu$l of protein loading buffer was added. The tubes were heated at 100° C. for 5 minutes and 15 $\mu$l was loaded on a 10% PAGE gel (BioRad, Cambridge, Mass.) and electrophoresed. Following electrophoresis, the gel was transferred to nitrocellulose, and Western blotting was carried out using peroxidase conjugated mouse monoclonal anti-myc antibody (1:2000 dilution) (Boehringer Mannheim, Indianapolis Ind.). The blot was visualized using the ECL system.

EXAMPLE 1

IDENTIFICATION OF EMI1 CDNA

In this example, a yeast two-hybrid assay was performed in which a plasmid containing a GAL4 DNA-binding domain-fchd540 gene fusion was introduced into the yeast two-hybrid screening strain HF7c described above. HF7c was then transformed with the human breast two-hybrid library. Five million transformants were obtained and plated in selection medium. Colonies that grew in the selection medium and expressed the beta-galactosidase reporter gene were further characterized and subjected to retransformation and specificity assays. The retransformation and specificity tests yielded one clone, EMI1, which was able to bind to selected MADR proteins.

The fchd540 gene coding sequence was amplified by PCR and cloned into pGBT9 creating a GAL4 DNA-binding domain-fchd540 gene fusion (plasmid pMB155). HF7c was transformed with this construct resulting in strain TB35. TB35 grew on synthetic complete medium lacking L-tryptophan but not on synthetic complete medium lacking L-tryptophan and L-histidine demonstrating that the GAL4 DNA-binding domain-fchd540 gene fusion does not have intrinsic transcriptional activation activity.

TB35 was transformed with the human breast two-hybrid library and 5 million transformants were obtained. The transformants were plated on synthetic complete medium lacking L-leucine, L-tryptophan, and L-histidine. Yeast colonies that grew on synthetic complete medium lacking L-leucine, L-tryptophan, and L-histidine as well as expressed the beta-galactosidase reporter gene were identified. The 30 strains with the strongest beta-galactosidase induction were characterized. Library plasmids were isolated from the 30 strains, and the 5' ends of all of the cDNA inserts were sequenced. This sequencing revealed that one cDNA had been identified twice and the other 28 cDNAs had been identified once. It is possible that some of the 28 cDNAs that appear to be unique are in fact portions of the same gene but, because of different fusion junctions to the vector, their sequences do not align with each other.

The 29 potentially unique cDNAs were subjected to retransformation and specificity tests. It was determined, using the yeast two-hybrid system, whether each library cDNA-encoded protein could physically interact with a panel of bait proteins which included the fchd540 gene product (MADR7), the fchd534 gene product (MADR6), the Drosophila MAD gene product, the DPC4 gene product, the p53 gene product, and the GAL4 DNA-binding domain. Yeast expression plasmids described above, which encode the GAL4 DNA-binding domain either alone or fused in-frame to the fchd540 gene (MADR7), the fchd534 gene (MADR6), the Drosophila MAD gene, the DPC4 gene, and p53 gene, were transformed into MATa two-hybrid screening strain HF7c. Yeast expression plasmids encoding GAL4 activation domain fusions to the 29 cDNAs and SV40 were transformed into MATα two-hybrid screening strain Y187. p53 and SV40 interact with each other and should not interact with the experimental proteins. The HF7c transformants were propagated as stripes on semisolid synthetic complete medium lacking L-tryptophan and the Y187 transformants were grown as stripes on semisolid synthetic complete medium lacking L-leucine. Both sets of stripes were replica plated in the form of a grid onto a single rich YPAD plate and the haploid strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-leucine, L-tryptophan, and L-histidine to assay HIS3 expression and a paper filter on a synthetic complete plate lacking L-leucine and L-tryptophan. The next day, the paper filter was subjected to the paper filter beta-galactosidase assay to measure expression of the lacZ reporter gene. HIS3 expression was scored after 3 days of growth at 30° C.

One clone, EMI1 encoded a polypeptide that interacted strongly with the fchd540 gene product (MADR7), the fchd534 gene product (MADR6), and the Drosophila MAD gene product but did not interact with other baits in the panel. The results of the retransformation and specificity test performed on EMI1 are summarized Table 4. The strength or absence of physical interaction between each combination of test proteins is listed. Strong interactions are defined as interactions that cause the activation of both the HIS3 and lacZ reporter genes.

TABLE 4

Summary of EMI1 Retransformation and Specificity Assays

| cDNA-GAL4 Activation Domain Fusion Tested | | |
|---|---|---|
| GAL4 DNA-Binding Domain Fusions | EMI1 | SV40 |
| fchd540 gene product (MADR7) | strong | none |
| fchd534 gene product (MADR6) | strong | none |
| Drosophila MAD gene product | strong | none |
| DPC4 gene product | none | none |
| p53 gene product | none | strong |
| GAL4 binding domain alone | none | none |
| PY motif of the fchd540 gene product (MADR7) | strong | none |
| P10→A10 mutant PY motif of the fchd540 gene product (MADR7) | none | none |
| Y12→A12 mutant PY motif of the fchd540 gene product (MADR7) | none | none |

Specific binding of the EMI1 gene product to three distinct MADR proteins (MADR7, MADR6, Drosophila MAD gene product) indicated that EMI1 is involved in a signaling pathway which involves an MADR protein. The complete DNA sequence of the EMI1 cDNA insert was determined using standard techniques. In brief, using a standard PCR strategy, the 5' missing portion of the EMI1 clone was amplified out of the human breast library. The 5' end of EMI1 was spliced onto the 3' end of EMI1 to create a full length EMI1 clone, the sequence of which was then determined and analyzed. All sequencing was performed by standard automated fluorescent dideoxynucleotide sequencing using dye primer chemistry (Applied Biosystems, Inc., Foster City, Calif.) on Applied Biosystems 373 and 377 sequenators. The DNA sequences were screened to eliminate bacterial, ribosomal, and mitochondrial contaminants. Sequence artifacts were also eliminated, such as vectors and repetitive elements.

EXAMPLE 2

EXPRESSION OF RECOMBINANT EMI1 PROTEIN IN BACTERIAL CELLS

In this example, EMI1 was expressed as a recombinant glutathione-S-transferase (GST) fusion protein in E. coli and the fusion protein was isolated and characterized. Specifically, as described above, EMI1 was fused to GST and this fusion protein was expressed in E. coli strain PEB199. As EMI1 was predicted to be 21 kD and GST was predicted to be 26 kD, the fusion protein was predicted to be 47 kD in molecular weight. Expression of the GST-EMI1 fusion protein in PEB 199 was induced with IPTG. The recombinant fusion protein was purified from crude bacterial lysates of the induced PEB 199 strain by affinity chromatography on glutathione beads. Using polyacrylamide gel electrophoretic analysis of the proteins purified from the bacterial lysates, the resultant fusion protein was determined to be 47 kD in size.

EXAMPLE 3

EXPRESSION OF RECOMBINANT EMI1 PROTEIN IN COS CELLS

To express the EMI1 gene in COS cells, the pcDNA/Amp vector by Invitrogen Corporation (San Diego, Calif.) is used.

This vector contains an SV40 origin of replication, an ampicillin resistance gene, an E. coli replication origin, a CMV promoter followed by a polylinker region, and an SV40 intron and polyadenylation site. A DNA fragment encoding the entire EMI1 protein and a HA tag (Wilson et al. (1984) Cell 37:767) fused in-frame to its 3' end of the fragment is cloned into the polylinker region of the vector, thereby placing the expression of the recombinant protein under the control of the CMV promoter.

To construct the plasmid, the EMI1 DNA sequence is amplified by PCR using two primers. The 5' primer contains the restriction site of interest followed by approximately twenty nucleotides of the EMI1 coding sequence starting from the initiation codon; the 3' end sequence contains complementary sequences to the other restriction site of interest, a translation stop codon, the HA tag and the last 20 nucleotides of the EMI1 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the EMI1 gene is inserted in the correct orientation. The ligation mixture is transformed into E. coli cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the EMI1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the EMI1 protein is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or 35Scysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated proteins are then analyzed by SDS-PAGE.

Alternatively, DNA containing the EMI1 coding sequence is cloned directly into the polylinker of the pCDNA/Amp vector using the appropriate restriction sites. The resulting plasmid is transfected into COS cells in the manner described above, and the expression of the EMI1 protein is detected by radiolabelling and immunoprecipitation using an EMI1 specific monoclonal antibody

EXAMPLE 4

CHARACTERIZATION OF EMI1 PROTEIN

In this example, the amino acid sequence of the EMI1 protein was compared to amino acid sequences of known proteins and various motifs were identified. In addition, using two hybrid screening assays, the ability of the EMI1 protein to interact with a panel of MADR proteins was analyzed.

The EMI1 protein, the amino acid sequence of which is shown in FIG. 1 (SEQ ID NO:2), is a novel protein which includes 335 amino acid residues. At its carboxyl terminus (amino acid residues 300–335), the EMI1 protein includes a 36 amino acid WW domain. WW domains have been reported to comprise a motif of approximately 38 amino acid residues, one of the prominent features of which is the presence of two conserved tryptophans (W) (Sudol et al. (1995) *FEBS Letters* 369:67–71). A WW domain consensus sequence can be found in the EMI1 protein depicted in SEQ ID NO:2 from amino acid residues 300 to 335 and in SEQ ID NO:4.

The EMI1 WW domain is most similar to the WW domains found in several ubiquitin protein ligases including mammalian NEDD4 (Staub et al. (1996) *EMBO J.* 15:2371–2380) and yeast RSP5 (GenBank™ Accession Number U18916:36076–38595). The highest similarity is 21/36 amino acid identities. However, EMI1 does not contain a hect domain, the catalytic site of ubiquitin protein ligases (Huibregtse et al. (1995) *PNAS* 92:2503–2507), suggesting that EMI1 is not a ubiquitin protein ligase. EMI1 may regulate protein stability by competing with ubiquitin protein ligases for PY domains, a WW consensus binding domain described below. This is tested by determining if WW domains present in ubiquitin protein ligases bind to the same PY motifs as the WW domain in EMI1.

The consensus sequence bound by the WW domain has been identified and designated as the PY motif (Chen and Sudol (1995) *PNAS* 92:7819–7823). The PY motif includes a proline-rich domain followed by a tyrosine residue. The particular PY motifs to which the WW domain binds include the following amino acid sequence: XPPXY (SEQ ID NO:16) wherein X can be any amino acid residue. Proteins known to include PY motifs include several members of the MADR family of proteins at least some members of which have been characterized as being effectors of the TGFβ response in cells. Examples of members of the MADR proteins are described herein. The PY motifs of some MADR proteins are shown below in Table 5:

TABLE 5

PY Motifs of Some MADR Proteins

| MAD Protein (amino acid residues) | PY Consensus: -------XPPXY (SEQ ID NO:16)---- | Source Chen and Sudol (1995) PNAS 92:7819–7823. |
|---|---|---|
| fchd540 gene product (MADR7) (aa 200 to aa 215) | RLCELESPPPPYSRYP (SEQ ID NO:8) | United States Serial No. 08/799,910, filed February 13, 1997. |

TABLE 5-continued

PY Motifs of Some MADR Proteins

| MAD Protein (amino acid residues) | PY Consensus: -------XPPXY (SEQ ID NO:16)---- | Source Chen and Sudol (1995) PNAS 92:7819–7823. |
|---|---|---|
| fchd534 gene product (MADR6) (aa 7 to aa 22) | PIETQKSPPPPYSRLS (SEQ ID NO:11) | United States Serial No. 08/599,654, filed February 9, 1996. |
| hMAD-1 (aa 216 to aa 231) | FQMPADTPPPAYLPPE (SEQ ID NO:12) | Zhang, Y. et al. (1996) Nature 383:168–172. |
| hMAD-2 (aa 214 to aa 229) | SNYIPETPPPGYISED (SEQ ID NO:13) | Zhang, Y. et al. (1996) Nature 383:168–172. |
| hMAD-3 (aa 172 to aa 187) | QSNIPETPPPGYLSED (SEQ ID NO:14) | Zhang, Y. et al. (1996) Nature 383:168–172. |
| Smad5 (aa 215 to aa 230) | FQLPADTPPPAYMPPD (SEQ ID NO:15) | Riggins, G. J. et al. (1996) Nat. Genetics 13:347–349. |
| Drosophila MAD (aa 214 to aa 229) | YDSLAGTPPPAYSPSE (SEQ ID NO:16) | Sekelsky, J. J. et al. (1995) Genetics 139:1347–1358. |

To confirm that the PY domain of the fchd540 gene product (MADR7) was the region of the fchd540 gene product (MADR7) that interacts with EMI1, two complementary oligonucleotides encoding the 16 amino acid PY domain of the fchd540 gene product (MADR7) (RLCELESPPPPYSRYP (SEQ ID NO:8)) were synthesized, annealed to each other, and cloned into the GAL4 DNA-binding domain fusion vector pGBT9 to create an fchd540 gene product (MADR7) PY bait construct. This construct was introduced into the two-hybrid screening strain HF7c resulting in strain TB39. Strain TB39 was added to the specificity testing panel described above in Example 1. The results of this specificity testing revealed that EMI1 interacted equally strongly with the full length 426 amino acid fchd540 gene product (MADR7) protein bait as with the 16 amino acid PY domain of the fchd540 gene product (MADR7) bait. This result establishes that EMI1 interacts specifically with the PY domain of the fchd540 gene product (MADR7).

PY domain baits (16 amino acids in length) which express mutant derivatives of the fchd540 gene product (MADR7) PY domain were then constructed. Plasmid pMB 147 encodes the 16 amino acid PY domain of the fchd540 gene product (MADR7) in which the proline at position 10 is mutated to alanine. Plasmid pMB148 encodes the 16 amino acid PY domain of the fchd540 gene product (MADR7) in which the tyrosine at position 12 is mutated to alanine. Analogous mutations in other PY domains have been shown to abolish specific binding of PY domains to their cognate WW domains (Chen and Sudol (1995) *PNAS* 92:7819–7823). pMB147 and pMB148 were introduced into HF7c by transformation creating TB40 and TB41, respectively. Western blotting confirmed that the transformants expressed both of the mutant PY domain baits. TB40 and TB41 were added to the specificity testing panel described above in Example 1. Specificity testing with TB40 and TB41 revealed that both the P10→A10 and Y12→A12 mutations abolished binding of the PY domain of the fchd540 gene product (MADR7) to EMI1 (Table 4). These results demonstrate that the 16 amino acid PY motif of the fchd540 gene product (MADR7) binds strongly to EMI1 and that two different amino acid substitutions known to prevent specific PY domain binding to WW domains block binding of the PY domain of the fchd540 gene product (MADR7) to EMI1. Taken together, these results show that the PY domain of the fchd540 gene product (MADR7) binds strongly and specifically to EMI1 and that EMI1 is, therefore, a regulator of fchd540 gene product (MADR7) activity.

To determine if EMI1 associates with the fchd534 gene product (MADR6) and the fchd540 gene product (MADR7) in endothelial cells, coimmunoprecipitation studies were performed. Primary BAECs were cotransfected with pN8epsilon-fchd534 (MADR6)-myc and pN8epsilon-EMI1-HA or pN8epsilon-fchd540 (MADR7)-myc and pN8epsilon-EMI1 -HA. Anti-HA antibodies were used in the immunoprecipitation step and proteins that were precipitated by the antibodies were electrophoresed, blotted, and probed with anti-myc antibodies in a Western blotting experiment. The results of the Western blotting experiment showed that both the fchd534 gene product (MADR6) and the fchd540 gene product (MADR7) coimmunoprecipitated with EMI1.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising the nucleotide sequence of SEQ ID NO:1 or the complement thereof.

2. An isolated nucleic acid molecule comprising the nucleotide sequence of SEQ ID NO:3 or the complement thereof.

3. An isolated nucleic acid molecule comprising the nucleotide sequence of the DNA insert of the plasmid deposited with ATCC as Accession Number 98375 or the complement thereof.

4. An isolated nucleic acid molecule comprising the coding region of the nucleotide sequence of SEQ ID NO:1 or the complement thereof.

5. An isolated nucleic acid molecule encoding the amino acid sequence of SEQ ID NO-2, or the complement thereof.

6. An isolated nucleic acid molecule encoding a SEQ ID NO:2 fusion protein, or the complement thereof.

7. An isolated nucleic acid molecule comprising a naturally-occurring allelic variant of the nucleotide sequence of SEQ ID NO:1, or the complement thereof.

8. A vector comprising the isolated nucleic acid molecule of any one of claims 1, 2, 3, 4, 5, 6, or 7.

9. The vector of claim 8, which is a recombinant expression vector.

10. A host cell containing the recombinant expression vector of claim 9.

11. A host cell containing the vector of claim 8.

12. A method for expressing a polypeptide, comprising transforming a host cell with the vector of claim 8, and culturing said host cell in a suitable medium such that said polypeptide is expressed.

13. The method of claim 12, further comprising isolating said polypeptide from the medium of the host cell.

14. An isolated nucleic acid molecule consisting of the nulcleotide sequence of SEQ ID NO:1, or the complement thereof.

15. An isolated nucleic acid molecule consisting of the nucleotide sequence of SEQ ID NO:3, or the complement thereof.

16. An isolated nucleic acid molecule consisting of the nucleotide sequence of the DNA insert of the plasmid deposited with ATCC as Accession Number 98375, or the complement thereof.

17. An isolated nucleic acid molecule consisting of a naturally-occurring allelic variant of the nucleotide sequence of SEQ ID NO:1, or the complement thereof.

* * * * *

UNITED STATES PATENT AND TRADEMARK OFFICE
CERTIFICATE OF CORRECTION

PATENT NO. : 5,948,639
DATED : September 7, 1999
INVENTOR(S) : Carlos J. Gimeno et al.

It is certified that error appears in the above-identified patent and that said Letters Patent is hereby corrected as shown below:

At column 67, line 41 please delete "SEQ ID NO-2" and insert
- - SEQ ID NO:2 - -.

Signed and Sealed this

Twenty-third Day of May, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 1290 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 77..1081

(xi) SEQUENCE DESCRIPTION: SEQ ID NO:1:

```
TGCGGGCGGT GGAAGGCGGA AGTAGGAGAG GAGTTCGGCG CCGCTTCTGT GGCCACGGCA          60

GCTTCACGGT GATGAT ATG GCA TCT GCC AGC TCT AGC CGG GCA GGA GTG            109
               Met Ala Ser Ala Ser Ser Ser Arg Ala Gly Val
                 1               5                  10

GCC CTG CCT TTT GAG AAG TCT CAG CTC ACT TTG AAA GTG GTG TCC GCA          157
Ala Leu Pro Phe Glu Lys Ser Gln Leu Thr Leu Lys Val Val Ser Ala
              15                  20                  25

AAG CCC AAG GTG CAT AAT CGT CAA CCG CGA ATT AAC TCC TAC GTG GAG          205
Lys Pro Lys Val His Asn Arg Gln Pro Arg Ile Asn Ser Tyr Val Glu
         30                  35                  40

GTG GCG GTG GAT GGA CTC CCC AGT GAG ACC AAG AAG ACT GGG AAG CGC          253
Val Ala Val Asp Gly Leu Pro Ser Glu Thr Lys Lys Thr Gly Lys Arg
     45                  50                  55

ATT GGG AGC TCT GAG CTT CTC TGG AAT GAG ATC ATC ATT TTG AAT GTT          301
Ile Gly Ser Ser Glu Leu Leu Trp Asn Glu Ile Ile Ile Leu Asn Val
 60                  65                  70                  75

ACG GCA CAG AGT CAT TTA GAT TTA AAG GTC TGG AGC TGC CAT ACC TTG          349
Thr Ala Gln Ser His Leu Asp Leu Lys Val Trp Ser Cys His Thr Leu
                 80                  85                  90

AGA AAT GAA CTG CTA GGC ACC GCA TCT GTC AAC CTC TCC AAC GTC TTG          397
Arg Asn Glu Leu Leu Gly Thr Ala Ser Val Asn Leu Ser Asn Val Leu
             95                 100                 105

AAG AAC AAT GGG GGC AAA ATG GAG AAC ATG CAG CTG ACC CTG AAC CTG          445
Lys Asn Asn Gly Gly Lys Met Glu Asn Met Gln Leu Thr Leu Asn Leu
         110                 115                 120

CAG ACG GAG AAC AAA GGC AGC GTT GTC TCA GGC GGA GAG CTG ACA ATT          493
Gln Thr Glu Asn Lys Gly Ser Val Val Ser Gly Gly Glu Leu Thr Ile
     125                 130                 135

TTC CTG GAC GGG CCA ACT GTT GAT CTG GGA AAT GTG CCT AAT GGC AGT          541
Phe Leu Asp Gly Pro Thr Val Asp Leu Gly Asn Val Pro Asn Gly Ser
140                 145                 150                 155

GCC CTG ACA GAT GGA TCA CAG CTG CCT TCG AGA GAC TCC AGT GGA ACA          589
Ala Leu Thr Asp Gly Ser Gln Leu Pro Ser Arg Asp Ser Ser Gly Thr
                 160                 165                 170

GCA GTA GCT CCA GAG AAC CGG CAC CAG CCC CCC AGC ACA AAC TGC TTT          637
Ala Val Ala Pro Glu Asn Arg His Gln Pro Pro Ser Thr Asn Cys Phe
             175                 180                 185

GGT GGA AGA TCC CGG ACG CAC AGA CAT TCG GGT GCT TCA GCC AGA ACA          685
Gly Gly Arg Ser Arg Thr His Arg His Ser Gly Ala Ser Ala Arg Thr
         190                 195                 200
```

-continued

```
ACC CCA GCA ACC GGC GAG CAA AGC CCC GGT GCT CGG AGC CGG CAC CGC        733
Thr Pro Ala Thr Gly Glu Gln Ser Pro Gly Ala Arg Ser Arg His Arg
205                 210                 215

CAG CCC GTC AAG AAC TCA GGC CAC AGT GGC TTG GCC AAT GGC ACA GTG        781
Gln Pro Val Lys Asn Ser Gly His Ser Gly Leu Ala Asn Gly Thr Val
220                 225                 230                 235

AAT GAT GAA CCC ACA ACA GCC ACT GAT CCC GAA GAA CCT TCC GTT GTT        829
Asn Asp Glu Pro Thr Thr Ala Thr Asp Pro Glu Glu Pro Ser Val Val
                240                 245                 250

GGT GTG ACG TCC CCA CCT GCT GCA CCC TTG AGT GTG ACC CCG AAT CCC        877
Gly Val Thr Ser Pro Pro Ala Ala Pro Leu Ser Val Thr Pro Asn Pro
                255                 260                 265

AAC ACG ACT TCT CTC CCT GCC CCA GCC ACA CCG GCT GAA GGA GAG GAA        925
Asn Thr Thr Ser Leu Pro Ala Pro Ala Thr Pro Ala Glu Gly Glu Glu
                270                 275                 280

CCC AGC ACT TCG GGT ACA CAG CAG CTC CCA GCG GCT GCC CAG GCC CCC        973
Pro Ser Thr Ser Gly Thr Gln Gln Leu Pro Ala Ala Ala Gln Ala Pro
285                 290                 295

GAC GCT CTG CCT GCT GGA TGG GAA CAG CGA GAG CTG CCC AAC GGA CGT       1021
Asp Ala Leu Pro Ala Gly Trp Glu Gln Arg Glu Leu Pro Asn Gly Arg
300                 305                 310                 315

GTC TAT TAT GTT GAC CAC AAT ACC AAG ACC ACC ACC TGG GAG CGG CCC       1069
Val Tyr Tyr Val Asp His Asn Thr Lys Thr Thr Thr Trp Glu Arg Pro
                320                 325                 330

CTT CCT CCA GGG TAGGTCATCA ACTGAGAAGA CCTGAGACTC TGGAACTGAC           1121
Leu Pro Pro Gly
                335

ACCATGAGTC ACCCAATGGC TTCTTGAAAC GGTCCCTTTC TGCGGAGGTA GCATAGCACA     1181

GTGACGTTTA TTCCGGGTCA CTTGATTGCT TTTCCTATCC ACTTACCTTA ATATTGCTCC     1241

CATGTCTTAG GACATATTAG AATTATTAGA AGATCTCTGG GAAACAAAA                 1290

(2) INFORMATION FOR SEQ ID NO:2:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Ala Ser Ser Ser Arg Ala Gly Val Ala Leu Pro Phe Glu
1               5                   10                  15

Lys Ser Gln Leu Thr Leu Lys Val Val Ser Ala Lys Pro Lys Val His
                20                  25                  30

Asn Arg Gln Pro Arg Ile Asn Ser Tyr Val Glu Val Ala Val Asp Gly
            35                  40                  45

Leu Pro Ser Glu Thr Lys Lys Thr Gly Lys Arg Ile Gly Ser Ser Glu
        50                  55                  60

Leu Leu Trp Asn Glu Ile Ile Ile Leu Asn Val Thr Ala Gln Ser His
65                  70                  75                  80

Leu Asp Leu Lys Val Trp Ser Cys His Thr Leu Arg Asn Glu Leu Leu
                85                  90                  95

Gly Thr Ala Ser Val Asn Leu Ser Asn Val Leu Lys Asn Gly Gly
            100                 105                 110

Lys Met Glu Asn Met Gln Leu Thr Leu Asn Leu Gln Thr Glu Asn Lys
        115                 120                 125

Gly Ser Val Val Ser Gly Gly Glu Leu Thr Ile Phe Leu Asp Gly Pro
    130                 135                 140
```

```
Thr Val Asp Leu Gly Asn Val Pro Asn Gly Ser Ala Leu Thr Asp Gly
145                 150                 155                 160

Ser Gln Leu Pro Ser Arg Asp Ser Ser Gly Thr Ala Val Ala Pro Glu
                165                 170                 175

Asn Arg His Gln Pro Pro Ser Thr Asn Cys Phe Gly Gly Arg Ser Arg
            180                 185                 190

Thr His Arg His Ser Gly Ala Ser Ala Arg Thr Thr Pro Ala Thr Gly
        195                 200                 205

Glu Gln Ser Pro Gly Ala Arg Ser Arg His Arg Gln Pro Val Lys Asn
    210                 215                 220

Ser Gly His Ser Gly Leu Ala Asn Gly Thr Val Asn Asp Glu Pro Thr
225                 230                 235                 240

Thr Ala Thr Asp Pro Glu Pro Ser Val Val Gly Val Thr Ser Pro
                245                 250                 255

Pro Ala Ala Pro Leu Ser Val Thr Pro Asn Pro Asn Thr Thr Ser Leu
                260                 265                 270

Pro Ala Pro Ala Thr Pro Ala Glu Gly Glu Pro Ser Thr Ser Gly
                275                 280                 285

Thr Gln Gln Leu Pro Ala Ala Ala Gln Ala Pro Asp Ala Leu Pro Ala
    290                 295                 300

Gly Trp Glu Gln Arg Glu Leu Pro Asn Gly Arg Val Tyr Tyr Val Asp
305                 310                 315                 320

His Asn Thr Lys Thr Thr Thr Trp Glu Arg Pro Leu Pro Pro Gly
                325                 330                 335

(2) INFORMATION FOR SEQ ID NO:3:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1005

(xi) SEQUENCE DESCRIPTION: SEQ ID NO:3:

ATG GCA TCT GCC AGC TCT AGC CGG GCA GGA GTG GCC CTG CCT TTT GAG      48
Met Ala Ser Ala Ser Ser Ser Arg Ala Gly Val Ala Leu Pro Phe Glu
1               5                   10                  15

AAG TCT CAG CTC ACT TTG AAA GTG GTG TCC GCA AAG CCC AAG GTG CAT      96
Lys Ser Gln Leu Thr Leu Lys Val Val Ser Ala Lys Pro Lys Val His
            20                  25                  30

AAT CGT CAA CCG CGA ATT AAC TCC TAC GTG GAG GTG GCG GTG GAT GGA     144
Asn Arg Gln Pro Arg Ile Asn Ser Tyr Val Glu Val Ala Val Asp Gly
        35                  40                  45

CTC CCC AGT GAG ACC AAG AAG ACT GGG AAG CGC ATT GGG AGC TCT GAG     192
Leu Pro Ser Glu Thr Lys Lys Thr Gly Lys Arg Ile Gly Ser Ser Glu
    50                  55                  60

CTT CTC TGG AAT GAG ATC ATC ATT TTG AAT GTT ACG GCA CAG AGT CAT     240
Leu Leu Trp Asn Glu Ile Ile Ile Leu Asn Val Thr Ala Gln Ser His
65                  70                  75                  80

TTA GAT TTA AAG GTC TGG AGC TGC CAT ACC TTG AGA AAT GAA CTG CTA     288
Leu Asp Leu Lys Val Trp Ser Cys His Thr Leu Arg Asn Glu Leu Leu
                85                  90                  95
```

```
GGC ACC GCA TCT GTC AAC CTC TCC AAC GTC TTG AAG AAC AAT GGG GGC        336
Gly Thr Ala Ser Val Asn Leu Ser Asn Val Leu Lys Asn Asn Gly Gly
            100                 105                 110

AAA ATG GAG AAC ATG CAG CTG ACC CTG AAC CTG CAG ACG GAG AAC AAA        384
Lys Met Glu Asn Met Gln Leu Thr Leu Asn Leu Gln Thr Glu Asn Lys
            115                 120                 125

GGC AGC GTT GTC TCA GGC GGA GAG CTG ACA ATT TTC CTG GAC GGG CCA        432
Gly Ser Val Val Ser Gly Gly Glu Leu Thr Ile Phe Leu Asp Gly Pro
    130                 135                 140

ACT GTT GAT CTG GGA AAT GTG CCT AAT GGC AGT GCC CTG ACA GAT GGA        480
Thr Val Asp Leu Gly Asn Val Pro Asn Gly Ser Ala Leu Thr Asp Gly
145                 150                 155                 160

TCA CAG CTG CCT TCG AGA GAC TCC AGT GGA ACA GCA GTA GCT CCA GAG        528
Ser Gln Leu Pro Ser Arg Asp Ser Ser Gly Thr Ala Val Ala Pro Glu
                165                 170                 175

AAC CGG CAC CAG CCC CCC AGC ACA AAC TGC TTT GGT GGA AGA TCC CGG        576
Asn Arg His Gln Pro Pro Ser Thr Asn Cys Phe Gly Gly Arg Ser Arg
            180                 185                 190

ACG CAC AGA CAT TCG GGT GCT TCA GCC AGA ACA ACC CCA GCA ACC GGC        624
Thr His Arg His Ser Gly Ala Ser Ala Arg Thr Thr Pro Ala Thr Gly
            195                 200                 205

GAG CAA AGC CCC GGT GCT CGG AGC CGG CAC CGC CAG CCC GTC AAG AAC        672
Glu Gln Ser Pro Gly Ala Arg Ser Arg His Arg Gln Pro Val Lys Asn
    210                 215                 220

TCA GGC CAC AGT GGC TTG GCC AAT GGC ACA GTG AAT GAT GAA CCC ACA        720
Ser Gly His Ser Gly Leu Ala Asn Gly Thr Val Asn Asp Glu Pro Thr
225                 230                 235                 240

ACA GCC ACT GAT CCC GAA GAA CCT TCC GTT GTT GGT GTG ACG TCC CCA        768
Thr Ala Thr Asp Pro Glu Glu Pro Ser Val Val Gly Val Thr Ser Pro
                245                 250                 255

CCT GCT GCA CCC TTG AGT GTG ACC CCG AAT CCC AAC ACG ACT TCT CTC        816
Pro Ala Ala Pro Leu Ser Val Thr Pro Asn Pro Asn Thr Thr Ser Leu
            260                 265                 270

CCT GCC CCA GCC ACA CCG GCT GAA GGA GAG GAA CCC AGC ACT TCG GGT        864
Pro Ala Pro Ala Thr Pro Ala Glu Gly Glu Glu Pro Ser Thr Ser Gly
            275                 280                 285

ACA CAG CAG CTC CCA GCG GCT GCC CAG GCC CCC GAC GCT CTG CCT GCT        912
Thr Gln Gln Leu Pro Ala Ala Ala Gln Ala Pro Asp Ala Leu Pro Ala
    290                 295                 300

GGA TGG GAA CAG CGA GAG CTG CCC AAC GGA CGT GTC TAT TAT GTT GAC        960
Gly Trp Glu Gln Arg Glu Leu Pro Asn Gly Arg Val Tyr Tyr Val Asp
305                 310                 315                 320

CAC AAT ACC AAG ACC ACC ACC TGG GAG CGG CCC CTT CCT CCA GGG              1005
His Asn Thr Lys Thr Thr Thr Trp Glu Arg Pro Leu Pro Pro Gly
                325                 330                 335

(2) INFORMATION FOR SEQ ID NO:4:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

Asp Ala Leu Pro Ala Gly Trp Glu Gln Arg Glu Leu Pro Asn Gly Arg
1               5                   10                  15

Val Tyr Tyr Val Asp His Asn Thr Lys Thr Thr Thr Trp Glu Arg Pro
            20                  25                  30
```

Leu Pro Pro Gly
     35

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGTCGAAGTG CCACTACTAT AC                                              22

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGTTCCAGAG TCTCAGG                                                    17

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ACGTCACTGT GCTATGCTAC                                                 20

(2) INFORMATION FOR SEQ ID NO:8:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:8:

Arg Leu Cys Glu Leu Glu Ser Pro Pro Pro Tyr Ser Arg Tyr Pro
 1               5                  10                  15

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

Arg Leu Cys Glu Leu Glu Ser Pro Pro Ala Pro Tyr Ser Arg Tyr Pro
 1               5                  10                  15

(2) INFORMATION FOR SEQ ID NO:10:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

```
Arg Leu Cys Glu Leu Glu Ser Pro Pro Pro Ala Ser Arg Tyr Pro
 1               5                  10                  15
```

(2) INFORMATION FOR SEQ ID NO:11:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:11:

```
Pro Ile Glu Thr Gln Lys Ser Pro Pro Pro Tyr Ser Arg Leu Ser
 1               5                  10                  15
```

(2) INFORMATION FOR SEQ ID NO:12:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:12:

```
Phe Gln Met Pro Ala Asp Thr Pro Pro Ala Tyr Leu Pro Pro Glu
 1               5                  10                  15
```

(2) INFORMATION FOR SEQ ID NO:13:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:13:

```
Ser Asn Tyr Ile Pro Glu Thr Pro Pro Gly Tyr Ile Ser Glu Asp
 1               5                  10                  15
```

(2) INFORMATION FOR SEQ ID NO:14:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:14:

```
Gln Ser Asn Ile Pro Glu Thr Pro Pro Gly Tyr Leu Ser Glu Asp
 1               5                  10                  15
```

(2) INFORMATION FOR SEQ ID NO:15:

```
      (i) SEQUENCE CHARACTERISTICS:
          (A) LENGTH: 16 amino acids
          (B) TYPE: amino acid
          (D) TOPOLOGY: linear (ii) MOLECULE TYPE: peptide (xi) SEQUENCE DESCRIPTION: SEQ ID NO:15:

Phe Gln Leu Pro Ala Asp Thr Pro Pro Pro Ala Tyr Met Pro Pro Asp
 1               5                  10                  15

(2) INFORMATION FOR SEQ ID NO:16:

(i) SEQUENCE CHARACTERISTICS:
          (A) LENGTH: 16 amino acids
          (B) TYPE: amino acid
          (D) TOPOLOGY: linear (ii) MOLECULE TYPE: peptide (xi) SEQUENCE DESCRIPTION: SEQ ID NO:16:

Tyr Asp Ser Leu Ala Gly Thr Pro Pro Pro Ala Tyr Ser Pro Ser Glu
 1               5                  10                  15
```